US008741858B2

(12) United States Patent
Ren et al.

(10) Patent No.: US 8,741,858 B2
(45) Date of Patent: Jun. 3, 2014

(54) OLIGOMER-NUCLEOSIDE PHOSPHATE CONJUGATES

(76) Inventors: Zhongxu Ren, Madison, AL (US);
Jennifer Riggs-Sauthier, Hunstville, AL (US); Timothy A. Riley, Hunstville, AL (US); Laurie A. VanderVeen, Los Altos, CA (US); Aaron S. Hammons, Huntsville, AL (US)

( * ) Notice: Subject to any disclaimer, the term of this patent is extended or adjusted under 35 U.S.C. 154(b) by 329 days.

(21) Appl. No.: 12/676,128

(22) PCT Filed: Sep. 18, 2008
(Under 37 CFR 1.47)

(86) PCT No.: PCT/US2008/010862
§ 371 (c)(1),
(2), (4) Date: May 21, 2010

(87) PCT Pub. No.: WO2009/042064
PCT Pub. Date: Apr. 2, 2009

(65) Prior Publication Data
US 2010/0286084 A1    Nov. 11, 2010

Related U.S. Application Data

(60) Provisional application No. 60/994,768, filed on Sep. 21, 2007.

(51) Int. Cl.
*A61K 31/70*      (2006.01)
*C07H 19/00*      (2006.01)

(52) U.S. Cl.
USPC .......................................... 514/42; 536/22.1

(58) Field of Classification Search
USPC ....................................................... 536/22.1
See application file for complete search history.

(56) References Cited

U.S. PATENT DOCUMENTS

| 2,697,709 A | 12/1954 | Hitchings et al. |
|---|---|---|
| 2,721,866 A | 10/1955 | Hitchings et al. |
| 2,800,473 A | 7/1957 | Hitchings et al. |
| 2,802,005 A | 8/1957 | Heidelberger et al. |
| 2,884,667 A | 5/1959 | Hitchings et al. |
| 2,885,396 A | 5/1959 | Heidelberger et al. |
| 2,949,451 A | 8/1960 | Hoffer |
| 2,970,139 A | 1/1961 | Duschinsky et al. |
| 3,019,224 A | 1/1962 | Hitchings et al. |
| 3,041,335 A | 6/1962 | Hoffer |
| 3,056,785 A | 10/1962 | Hitchings et al. |
| 3,116,282 A | 12/1963 | Hunter et al. |
| 3,132,144 A | 5/1964 | Hitchings et al. |
| 3,221,010 A | 11/1965 | Duschinsky et al. |
| 3,350,388 A | 10/1967 | Sorm et al. |
| 3,463,850 A | 8/1969 | Shen et al. |
| 3,923,785 A | 12/1975 | Ryder et al. |
| 3,991,045 A | 11/1976 | Ishida et al. |
| 4,071,519 A | 1/1978 | Ozaki et al. |
| 4,357,324 A | 11/1982 | Montgomery et al. |
| 4,503,045 A | 3/1985 | Fujii et al. |
| 4,751,221 A | 6/1988 | Watanabe et al. |
| 4,808,614 A | 2/1989 | Hertel |
| 4,918,179 A | 4/1990 | Watanabe et al. |
| 4,966,891 A | 10/1990 | Fujiu et al. |
| 4,983,609 A | 1/1991 | Fujii |
| 5,032,680 A | 7/1991 | Kawai et al. |
| 5,384,310 A | 1/1995 | Montgomery et al. |
| 5,472,949 A * | 12/1995 | Arasaki et al. .................. 514/49 |
| 5,661,136 A | 8/1997 | Montgomery et al. |
| 5,672,662 A | 9/1997 | Harris et al. |
| 5,681,811 A * | 10/1997 | Ekwuribe ...................... 514/7.4 |
| 6,191,105 B1 | 2/2001 | Ekwuribe et al. |
| 6,211,166 B1 | 4/2001 | Hattori et al. |
| 6,303,569 B1 | 10/2001 | Greenwald et al. |
| 6,680,382 B2 | 1/2004 | Bauta et al. |
| 6,936,597 B2 | 8/2005 | Greenwald et al. |
| 7,144,978 B2 | 12/2006 | Huang et al. |
| 2003/0165849 A1 | 9/2003 | Zhang et al. |
| 2005/0136031 A1 | 6/2005 | Bentley et al. |

FOREIGN PATENT DOCUMENTS

| WO | WO 97/21452 | 6/1997 |
|---|---|---|
| WO | WO 01/83502 | 11/2001 |
| WO | WO 02/098949 | 12/2002 |
| WO | Wo 2006/113615 | 10/2006 |

OTHER PUBLICATIONS

Bonora et al., Bioconjugate Chemistry, 1997, 8, 793-797.*
Budavari et al., The Merck Index, 1996, 12th edition, published by Merck Research Laboratories, 3 pages.*
Chen, et al., "Synthesis and Properties of ABA Amphiphiles," J. Org. Chem., vol.64, pp. 6870-6873, (1999).
Ertl, et al., "Fast Calculation of Molecular Polar Surface Area as a Sum of Fragment-Based Contributions and Its Application to the Prediction of Drug Transport Properties," J. Med. Chem., vol. 43, pp. 3714-3717, (2000).
Fiammengo, et al., "Efficient Preparation of Organic Subtrate-RNA Conjugates via in Vitro Transcription," J. Am. Chem. Soc., vol. 127, pp. 9271-9276, (2005).
Kelder, et al., "Polar Molecular Surface as a Dominating Determinant for Oral Absorption and Brain Penetration of Drugs," Pharm. Res., vol. 16, No. 10, pp. 1514-1519, (1999).
Lapis, et al., "Antiinvasive Effects of Tiazofurin on Liver-Metastatic Human colon Carcinoma Xenografts", Anticancer Res., vol. 16, pp. 3323-3332, (1996).
Liu, et al., "RNA-Mediated Synthesis of Palladium Nanoparticles on Au Surfaces," Langmuir, vol. 22, pp. 5862-5866, (2006).
Raso, et al., "Inhibition of the Progession of Human and Rat Wilms' Tumor by Tiazofurin", Anticancer Res., vol. 16, pp. 3333-3340, (1996).
Seelig, et al., "Site-Specific Modification of Enzymatically Synthesized RNA: Transcription Initiation and Diels-Alder Reaction," Tetrahedron Lett., vol. 38, No. 4, pp. 7729-7732, (1997).
Tovari, et al., "The Antitumor Effect of Tiazofurin (TR) Consists of Anti-Proliferative and Anti-Invasive Elements," Anticancer Res., vol. 16, pp. 3307-3312, (1996).
Tricot, et al., "Biochemically targeted therapy of refractory leukemia and myeloid blast crisis of chronic granulocytic leukemia with Tiazofurin, a selective blocker of inosine 5'-phoisate dehydrogenase activity", Anticancer Re., vol. 16, pp. 3341-3348, (1996).

(Continued)

Primary Examiner — Elli Peselev

(57) ABSTRACT

The invention provides small molecule drugs that are chemically modified by covalent attachment of a water soluble, non-peptidic oligomer. The conjugates of the invention, when administered by any of a number of administration routes, exhibits advantages over previously administered compounds.

12 Claims, No Drawings

(56) References Cited

OTHER PUBLICATIONS

Weber, et al., "Tiazofurin: Molecular and Clinical Action", Anticancer Res., vol. 16, pp. 3313-3322, (1996).

Wolf, et al., "Synthesis of guanosine 5'-conjugates and their use as initiator molecules for transcription priming," Org. Biomol. Chem., vol. 6, pp. 899-907, (2008).

Wright, et al., "Tiazofurin Effects on IMP-Dehydrogenase Activity and Expression in the Leukemia Cells of Patients with CML Blast Crisis", Anticancer Res., vol. 16, pp, 3349-3354, (1996).

Zajchowski, et al., "Anti-tumor efficacy of the nucleoside analog 1-(2-deoxy-2-fluoro-4-thio-β-D-arabinofuranosyl) cytosine (4'-thio-FAC) in human pancreatic and ovarian tumor xenograft models," Int. J. Cancer, vol. 114, pp. 1002-1009, (2005).

PCT International Search Report corresponding to PCT International Application No. PCT/US2008/010862 date of mailing Dec. 9, 2009.

PCT International Preliminary Report on Patentability corresponding to PCT International Application No. PCT/US2008/010862 date of issuance of report Mar. 24, 2010.

Enzon Pharmaceuticals, Macromolecular Engineering Technologies, pp. 1-14, (2004).

Nektar™ —Transforming Therapeutics, Nektar Molecule Engineering: Polyethylene Glycol and Derivatives for Advanced PEGylation, pp. 1-20, Catalog—2003, (Jul. 2003).

Nektar™ —Transforming Therapeutics, Nektar Advanced PEGylation: Polyethylene Glycol and Derivatives for Advanced PEGylation, pp. 1-24, Catalog—2004, (Jul. 2004).

Nektar™ —Transforming Therapeutics, Nektar Advanced PEGylation: Polyethylene Glycol and Derivatives for Advanced PEGylation, pp. 1-30, (Catalog 2005-2006).

NOF Corporation, "PEG Derivatives, Phospholipid and Drug Delivery Materials for Pharmaceuticals", pp. 1-46, Catalogue 2003-1st, (Jan. 2003).

NOF Corporation, "PEG Derivatives, Phospholipids and Drug Delivery Materials for Pharmaceuticals", pp. 1-50, Catalogue 2003-2nd, (Mar. 2004).

NOF Corporation, "PEG Derivatives, Phospholipods and Drug Delivery Materials for Pharmaceutical Products and Formulations", pp. 1-59, Catalogue Ver. 8, (Apr. 2006).

Polypure, Products; PEG amines; PEG acids and amino acids; PEG thiols and disulfides; Biotins, (Apr. 2004).

Polypure, Products; PEG amines; PEG acids and amino acids; PEG thiols and disulfides; Biotins, (Apr. 2005).

Quanta Biodesign, Labeling, Derivatization and Crosslinking Reagents for Biological and Related Materials with dPEG™ , pp. 1-38, (Mar. 12, 2004).

Quanta Biodesign, Labeling, Modification and Crosslinking Reagents incorporating our unique monodispersed dPEG™ Technology, pp, 1-31, (Nov. 5, 2004).

Quanta Biodesign, Ltd., Leading innovator, producer and provider of monodisperse discrete PEG™ (dPEG™) derivatives, (Product Catalog), pp. 1-51, (Updated: Jul. 18, 2005).

Quanta Biodesign, Ltd., Leading innovator, producer and provider of monodisperse discrete PEG™ (dPEG™) derivatives, (Product Catalog), pp, 1-51, (Updated: Nov. 17, 2005).

Shearwater Polymers, Inc., Polyethylene Glycol and Derivatives,pp. 1-49, (Catalog—Mar. 1995),.

Shearwater Polymers, Inc., Polyethylene Glycol and Derivatives, pp. 1-53, (Catalog—Jul. 1997).

Shearwater Polymers, Inc., Polyethylene Glycol and Derivatives: Functionalized Biocompatible Polymers for Research and Pharmaceuticals, pp. 1-50, (Catalog — Jan. 2000).

Shearwater Corporation, Polyethylene Glycol and Derivatives for Biomedical, Applications, pp. 1-17, (Catalog—Jul. 2001).

* cited by examiner

OLIGOMER-NUCLEOSIDE PHOSPHATE CONJUGATES

CROSS REFERENCE TO RELATED APPLICATIONS

This application is a 35 U.S.C. §371 application of International Application No. PCT/US2008/010862, filed Sep. 18, 2008, designating the United States, which claims the benefit of priority under 35 U.S.C. §119(e) to Provisional Application Ser. No. 60/994,768, filed 21 Sep. 2007, both of which are incorporated herein by reference in their entireties.

FIELD OF THE INVENTION

This invention provides (among other things) chemically modified nucleoside phosphates that possess certain advantages over nucleoside phosphates lacking the chemical modification. The chemically modified nucleoside phosphates described herein relate to and/or have application(s) in (among others) the fields of drug discovery, pharmacotherapy, physiology, organic chemistry and polymer chemistry.

BACKGROUND OF THE INVENTION

When a normal cell loses the ability to control its growth and division it is considered cancerous. Cancers or neoplasms have been reported from every tissue and cell type. These various cancers are normally treated using radiological and/or chemotherapeutic agents. These agents include a wide range of compounds and radioisotopes that work by various mechanisms. Although development has been directed toward agents capable of selective actions on neoplastic tissues, those available presently manifest significant toxicity on normal tissues as a major complication of therapy.

One class of antineoplastic agents is antimetabolites. A further subclass of antimetabolites includes inhibitors of DNA and RNA synthesis and inhibitors of nucleotide synthesis. Many of these are analogs of the naturally occurring nucleosides: adenosine; guanosine; uridine; cytidine; and thymidine. As these nucleoside analogs are inhibitors of DNA and/or RNA synthesis or nucleoside metabolism; these compounds are also useful for treating viral diseases like, including but not limited to, viral hepatitis, AIDS, common cold, rhinitis, and flu. However, their actions on the normal tissues result in side effects, including, but not limited to, anemia, leucopenia, neutropenia, thrombocytopenia, proteinuria, hematuria, vomiting, pain, fever, rash, dyspnea, constipation, diarrhea, hemorrhage, infection, alopecia, stomatitis, somnolence, paresthesias, chemical arachnoiditis, and neurotoxicity. Adverse events may include death. Thus, there is need in the art to provide improved nucleoside analogs for treatment of these diseases.

Additionally, Hepatitis C virus infection is one of the leading causes of chronic liver disease; more than 170 million people worldwide are infected, with HCV genotype 1 predominating in the US. The current standard of treatment consists of PEGylated interferon-α2 (pegIFN) alone or in combination with ribavirin. Combination treatment is effective in only 50% of patients with HCV genotype 1 infection, and some patients experience significant side effects in response to the treatment. Thus, there is considerable interest in the development of more effective agents with fewer side effects.

The present invention seeks to address these and other needs in the art by providing (among other things) a conjugate of a water-soluble, non-peptidic oligomer and nucleoside phosphate.

SUMMARY OF THE INVENTION

In one or more embodiments of the invention, compounds are provided; the compounds comprising a residue of a nucleoside phosphate covalently attached either directly or through one or more atoms, to a water-soluble, non-peptidic oligomer.

In one embodiment, a compound is provided comprising a residue of a nucleoside phosphate covalently attached, either directly or through one or more atoms, to a water-soluble, non-peptidic oligomer having an end-capping group selected from hydroxyl and carbon-containing end-capping groups.

In another embodiment, a compound is provided comprising a residue of a nucleoside phosphate covalently attached, either directly or through one or more atoms, to a water-soluble, non-peptidic oligomer having an end-capping group selected from hydroxyl and carbon-containing end-capping groups, having the following structure:

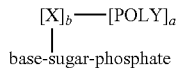

wherein:
base is a residue of a small molecule purine or pyrimidine base;
(a) is an integer having a value of one or two, inclusive;
(b) is an integer having a value of zero or one;
X is a linker when present; and
POLY is a water-soluble, non-peptidic oligomer having an end capping group selected from hydroxyl and carbon-containing end-capping groups.

In another embodiment, a compound is provided comprising a residue of a nucleoside phosphate covalently attached, either directly or through one or more atoms, to a water-soluble, non-peptidic oligomer having an end-capping group selected from hydroxyl and carbon-containing end-capping groups, having the following structure:

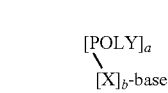

wherein:
base is a residue of a small molecule purine or pyrimidine base;
(a) is an integer having a value of one or two, inclusive;
(b) is an integer having a value of zero or one;
X is a linker when present; and
POLY is a water-soluble, non-peptidic oligomer having an end capping group selected from hydroxyl and carbon-containing end-capping groups.

In one or more embodiments, a compound is provided, the compound having the following structure:

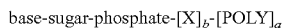

wherein:
base is a residue of a small molecule purine or pyrimidine base;

(a) is an integer having a value of one or two, inclusive;
(b) is an integer having a value of zero or one;
X is a linker when present; and
POLY is a water-soluble, non-peptidic oligomer having an end capping group selected from hydroxyl and carbon-containing end-capping groups.

In one or more embodiments, a compound is provided, the compound having the following structure:

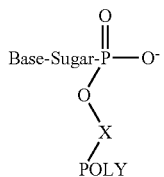

wherein:
base is a residue of a small molecule purine or pyrimidine base;
(a) is an integer having a value of one or two, inclusive;
(b) is an integer having a value of zero or one;
X is a linker when present; and
POLY is a water-soluble, non-peptidic oligomer having an end capping group selected from hydroxyl and carbon-containing end-capping groups.

In one or more embodiments, a compound is provided, the compound having the following structure:

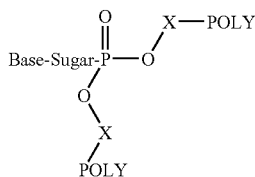

wherein:
base is a residue of a small molecule purine or pyrimidine base;
(a) is an integer having a value of one or two, inclusive;
(b) is an integer having a value of zero or one;
X is a linker when present; and
POLY is a water-soluble, non-peptidic oligomer having an end capping group selected from hydroxyl and carbon-containing end-capping groups.

In one or more embodiments, a compound is provided, the compound having the following structure:

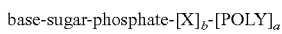

wherein:
base is a residue of a small molecule purine or pyrimidine base;
(a) is an integer having a value of one or two, inclusive;
(b) is an integer having a value of zero or one;
X is a linker when present; and
POLY, is a water-soluble, non-peptidic oligomer having an end capping group selected from hydroxyl and carbon-containing end-capping groups; with a proviso that the base or the sugar is non-naturally occurring.

In one or more embodiments of the invention, a compound is provided, the compound comprising a residue of a nucleoside phosphate covalently attached via a linker to a water-soluble, non-peptidic oligomer, wherein the nucleoside has a structure encompassed by Formula I.

In one or more embodiments of the invention, a compound is provided, the compound comprising a residue of a nucleoside phosphate covalently attached via a linker to a water-soluble, non-peptidic oligomer, wherein the nucleoside phosphate or the nucleoside has a structure encompassed by Formula II.

In one or more embodiments of the invention, a compound is provided, the compound comprising a residue of a nucleoside phosphate covalently attached via a linker to a water-soluble, non-peptidic oligomer, wherein the nucleoside phosphate or the nucleoside has a structure encompassed by Formula III.

In one or more embodiments of the invention, a compound is provided, the compound comprising a residue of a nucleoside phosphate covalently attached via a linker to a water-soluble, non-peptidic oligomer, wherein the nucleoside phosphate or the nucleoside has a structure encompassed by Formula IV.

In one or more embodiments of the invention, a compound is provided, the compound comprising a residue of a nucleoside phosphate covalently attached via a linker to a water-soluble, non-peptidic oligomer, wherein the nucleoside phosphate or the nucleoside has a structure encompassed by Formula V.

In one or more embodiments of the invention, a compound is provided, the compound comprising a residue of a nucleoside phosphate covalently attached via a linker to a water-soluble, non-peptidic oligomer, wherein the nucleoside phosphate or the nucleoside has a structure encompassed by Formula VI.

In one or more embodiments of the invention, a compound is provided, the compound comprising a residue of a nucleoside phosphate covalently attached via a linker to a water-soluble, non-peptidic oligomer, wherein the nucleoside phosphate or the nucleoside has a structure encompassed by Formula VII.

In one or more embodiments of the invention, a compound is provided, the compound comprising a residue of a nucleoside phosphate covalently attached via a linker to a water-soluble, non-peptidic oligomer, wherein the nucleoside phosphate or the nucleoside has a structure encompassed by Formula VIII.

In one or more embodiments of the invention, a compound is provided, the compound comprising a residue of a nucleoside phosphate covalently attached via a linker to a water-soluble, non-peptidic oligomer, wherein the nucleoside phosphate or the nucleoside has a structure encompassed by Formula IX.

In one or more embodiments of the invention, a compound is provided, the compound comprising a residue of a nucleoside phosphate covalently attached via a linker to a water-soluble, non-peptidic oligomer, wherein the nucleoside phosphate or the nucleoside has a structure encompassed by Formula X.

In one or more embodiments of the invention, a compound is provided, the compound comprising a residue of a nucleoside phosphate covalently attached via a linker to a water-soluble, non-peptidic oligomer, wherein the nucleoside phosphate or the nucleoside has a structure encompassed by Formula XI.

In one or more embodiments of the invention, a compound is provided, the compound comprising a residue of a nucleoside phosphate covalently attached via a linker to a water-soluble, non-peptidic oligomer, wherein the nucleoside phosphate or the nucleoside has a structure encompassed by Formula XII.

In one or more embodiments of the invention, a pharmaceutical composition is provided, the compound comprising a residue of a nucleoside phosphate covalently attached via a linker to a water-soluble, non-peptidic oligomer, and, optionally, a pharmaceutically acceptable excipient.

In one or more embodiments, a composition is provided, the composition having the following structure:

base-sugar-phosphate-$[X]_b$-$[POLY]_a$ wherein:
base is a residue of a small molecule purine or pyrimidine base;
(a) is an integer having a value of one or two, inclusive;
(b) is an integer having a value of zero or one;
X is a linker when present and in each occurrence;
POLY is a water-soluble, non-peptidic oligomer having an end capping group; and, optionally, a pharmaceutically acceptable excipient.

In one or more embodiments of the invention, a dosage form is provided, the dosage form comprising a compound having the following structure:

base-sugar-phosphate-$[X]_b$-$[POLY]_a$ wherein:
base is a residue of a small molecule purine or pyrimidine base;
(a) is an integer having a value of one or two, inclusive;
(b) is an integer having a value of zero or one;
X is a linker when present;
POLY is a water-soluble, non-peptidic oligomer having an end capping group.

In one or more embodiments of the invention, a method is provided, the method comprising administering a composition having the following structure:

base-sugar-phosphate-$[X]_b$-$[POLY]_a$ wherein:
base is a residue of a small molecule purine or pyrimidine base;
(a) is an integer having a value of one or two, inclusive;
(b) is an integer having a value of zero or one;
X is a linker when present;
POLY is a water-soluble, non-peptidic oligomer having an end capping group; and optionally, a pharmaceutically acceptable excipient.

These and other objects, aspects, embodiments and features of the invention will become more fully apparent when read in conjunction with the following detailed description.

BRIEF DESCRIPTION OF THE FIGURES

This paragraph intentionally left blank.

DETAILED DESCRIPTION OF THE INVENTION

It must be noted that, as used in this specification, the singular forms "a," "an," and "the" include plural referents unless the context clearly dictates otherwise.

In describing and claiming the present invention, the following terminology will be used in accordance with the definitions described below.

"Water soluble and non-peptidic oligomer" indicates an oligomer that is at least 35% (by weight) soluble, and preferably greater than 95% soluble, in water at room temperature. An unfiltered aqueous preparation of a "water-soluble" oligomer transmits at least 75%, more preferably at least 95%, of the amount of light transmitted by the same solution after filtering. On a weight basis, a "water soluble" oligomer is preferably at least 35% (by weight) soluble in water, more preferably at least 50% (by weight) soluble in water, still more preferably at least 70% (by weight) soluble in water, and still more preferably at least 85% (by weight) soluble in water. It is preferred, however, that the water-soluble oligomer is at least 95% (by weight) soluble in water or completely soluble in water.

The terms "monomer," "monomeric subunit" and "monomeric unit" are used interchangeably herein and refer to one of the basic structural units of a polymer or oligomer. In the case of a homo-oligomer, this is defined as a structural repeating unit of the oligomer. In the case of a co-oligomer, a monomeric unit is more usefully defined as the residue of a monomer which was oligomerized to form the oligomer, since the structural repeating unit may include more than one type of monomeric unit. Preferred oligomers of the invention are homo-oligomers.

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though the oligomer may contain distinct end capping moieties or functional groups, e.g., for conjugation. PEG oligomers for use in the present invention may comprise of following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG oligomers, the variable (n) ranges from 1 to 30, and the terminal groups and architecture of the overall PEG can vary. When PEG further comprises a functional group, A, for linking to, e.g., a small molecule drug, the functional group when covalently attached to a PEG oligomer, does not result in formation of (i) an oxygen-oxygen bond (—O—O—, a peroxide linkage), or (ii) a nitrogen-oxygen bond (N—O, O—N).

An "end capping group" is generally a non-reactive carbon-containing group attached to a terminal oxygen of a PEG oligomer. For the purposes of the present invention, preferred are capping groups having relatively low molecular weights such as methyl or ethyl. The end-capping group may also comprise a detectable label. Such labels include, without limitation, fluorescers, chemiluminescers, moieties used in enzyme labeling, colorimetric labels (e.g., dyes), metal ions, and radioactive moieties. Another end capping group is hydroxyl.

"Branched", in reference to the geometry or overall structure of an oligomer, refers to an oligomer having two or more polymer "arms" extending from a branch point.

"Forked" in reference to the geometry or overall structure of an oligomer, refers to an oligomer having two or more functional groups (through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof is meant to encompass protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, thiolesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds are found in standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, yet still more preferably with 99.99% or greater of some given quantity.

"Monodisperse" refers to an oligomer composition wherein substantially all of the oligomers in the composition have a well-defined, single (i.e., the same) molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the moiety derived from a small molecule drug. A composition comprised of monodisperse conjugates may, however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and even more preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and even more preferably a MW/Mn value of 1.0000 if the oligomer were not attached to the moiety derived from a small molecule drug. A composition comprised of bimodal conjugates may, however, include one or more nonconjugate substances such as solvents, reagents, excipients, and so forth A "nucleoside phosphate" refers to an organic, inorganic, or organometallic compound having a molecular weight of less than about 1000 Daltons and having some degree of activity as an antineoplastic agent or as an antiviral agent. In some embodiments of the invention a nucleoside or a nitrogenous base is described that may be converted to a desired nucleoside phosphate molecule using the techniques described herein as well as by the techniques known to one skilled in the art. Nucleoside phosphates of the invention may encompass nucleoside mono-, di-, and tri-phosphates, as well as oligopeptides, oligonucleotides, and other biomolecules having a molecular weight of less than about 1000.

A "biological membrane" is any membrane made of cells or tissues, that serves as a barrier to at least some foreign entities or otherwise undesirable materials. As used herein a "biological membrane" includes those membranes that are associated with physiological protective barriers including, for example: the blood-brain barrier; the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate," provides a measure of a compound's ability to cross a biological barrier, such as the blood-brain barrier ("BBB"). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known, described herein and/or in the relevant literature, and/or may be determined by one of ordinary skill in the art.

A "reduced rate of metabolism" refers to a measurable reduction in the rate of metabolism of a water-soluble oligomer-small molecule drug conjugate as compared to rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and may pass through the liver prior to reaching the systemic circulation. Because the liver is the primary site of drug metabolism or biotransformation, a substantial amount of drug may be metabolized before it reaches the systemic circulation. The degree of first pass metabolism, and thus, any reduction thereof, may be measured by a number of different approaches. For instance, animal blood samples may be collected at timed intervals and the plasma or serum analyzed by chromatography/mass spectrometry for metabolite levels. Other techniques for measuring a "reduced rate of metabolism" associated with the first pass metabolism and other metabolic processes are known, described herein and/or in the relevant literature, and/or may be determined by one of ordinary skill in the art. Preferably, a conjugate of the invention can provide a reduced rate of metabolism reduction satisfying at least one of the following values: at least about 5%, at least about 10%, at least about 15%; least about 20%; at least about 25%; at least about 30%; at least about 40%; at least about 50%; at least about 60%; at least about 70%; at least about 80%; and at least about 90%.

A compound (such as a small molecule drug or conjugate thereof) that is "orally bioavailable" is one that exhibits a bioavailability when administered orally of greater than 1%, and preferably greater than 10%, where a compound's bioavailability is the fraction of administered drug that reaches the systemic circulation in unmetabolized form.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Non-interfering substituents" are those groups that, when present in a molecule, are non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

"Links" of an alkyl group are referred to as alkylene, e.g., methylene, ethylene.

The term "substituted" is used throughout the specification. The term "substituted" is defined herein as "encompassing moieties or units that can replace a hydrogen atom, two hydrogen atoms, or three hydrogen atoms of a hydrocarbyl moiety. Also, substituted can include replacement of hydrogen atoms on two adjacent carbons to form a new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy and the like. Three hydrogen replacement includes cyano and the like. An epoxide unit is an example of a substituted unit that requires replacement of a hydrogen atom on adjacent carbons. The term substituted is used throughout the present specification to indicate that a hydrocarbyl moiety such as, inter alia, an aromatic ring or alkyl chain, can have one or more of the hydrogen atoms replaced by a substituent. When a moiety is described as "substituted," any number of the hydrogen atoms may be replaced. For example, 4-hydroxyphenyl is a "substituted aromatic carbocyclic ring," (N,N-dimethyl-5-amino) octanyl is a "substituted $C_8$ alkyl unit," 3-guanidinopropyl is a "substituted $C_3$ alkyl unit," and 2-carboxypyridinyl is a "substituted heteroaryl unit."

The following are non-limiting examples of units which can serve as a replacement for hydrogen atoms when a unit is described as "substituted."

i) —$[C(R^{20})_2]_p(CH=CH)_qR^{20}$; wherein p is from 0 to 12; q is from 0 to 12;
ii) —$C(Z)R^{20}$;
iii) —$C(Z)_2R^{20}$;
iv) —$C(Z)CH=CH_2$;
v) —$C(Z)N(R^{20})_2$;
vi) —$C(Z)NR^{20}N(R^{20})_2$;
vii) —CN;
viii) —CNO;
ix) —$CF_3$, —$CCl_3$, —$CBr_3$;
Z) —$N(R^{20})_2$;
xi) —$NR^{20}CN$;
xii) —$NR^{20}C(Z)R^{20}$;
xiii) —$NR^{20}C(Z)N(R^{20})_2$;
xiv) —$NHN(R^{20})_2$;
xv) —$NHOR^{20}$;
xvi) —NCS;
xvii) —$NO_2$;
xviii) —$OR^{20}$;
xix) —OCN;
xx) —$OCF_3$, —$OCCl_3$, —$OCBr_3$;
xxi) —F, —Cl, —Br, —I, and mixtures thereof;
xxii) —SCN;
xxiii) —$SO_3M$;
xxiv) —$OSO_3M$;
xxv) —$SO_2N(R^{20})_2$;
xxvi) —$SO_2R^{20}$;
xxvii) —$P(O)H_2$;
xxviii) —$PO_2$;
xxix) —$P(O)(OH)_2$;
xxx) and mixtures thereof;

wherein $R^{20}$ is hydrogen, substituted or unsubstituted $C_1$-$C_{20}$ linear, branched, or cyclic alkyl, $C_6$-$C_{20}$ aryl, and mixtures thereof; M is hydrogen, or a salt forming cation; Z is =O, =S, =$NR^{20}$, and mixtures thereof. Suitable salt forming cations include sodium, lithium, potassium, calcium, magnesium, ammonium, and the like.

"Electrophile" refers to an ion, atom, or an ionic or neutral collection of atoms having an electrophilic center, i.e., a center that is electron seeking, capable of reacting with a nucleophile.

"Nucleophile" refers to an ion or atom or an ionic or neutral collection of atoms having a nucleophilic center, i.e., a center that is seeking an electrophilic center, and capable of reacting with an electrophile.

"Pharmaceutically acceptable excipient" or "pharmaceutically acceptable carrier" refers to an excipient that may be included in the compositions of the invention and that causes no significant adverse toxicological effects to the patient.

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterodifunctional.

A basic or acidic reactant described herein includes neutral, charged, and any corresponding salt forms thereof.

The term "patient," refers to a living organism suffering from or prone to a condition that may be prevented or treated by administration of a conjugate as described herein and includes both humans and animals.

"Optional" or "optionally" means that the subsequently described circumstance may or may not occur, so that the description includes instances where the circumstance occurs and instances where it does not.

As indicated above, the present invention is directed to (among other things) a compound comprising a residue of a nucleoside phosphate covalently attached either directly or through one or more atoms, to a water-soluble, non-peptidic oligomer.

In one embodiment, a compound is provided comprising a residue of a nucleoside phosphate covalently attached, either directly or through one or more atoms, to a water-soluble, non-peptidic oligomer having an end-capping group selected from hydroxyl and carbon-containing end-capping groups.

In one embodiment, a compound is provided comprising a residue of a nucleoside phosphate covalently attached, either directly or through one or more atoms, to a water-soluble, non-peptidic oligomer having an end-capping group other than sulfur-containing end-capping groups.

In another embodiment, a compound is provided comprising a residue of a nucleoside phosphate covalently attached, either directly or through one or more atoms, to a water-soluble, non-peptidic oligomer having an end-capping group selected from hydroxyl and carbon-containing end-capping groups, having the following structure:

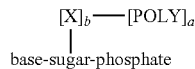

wherein:
base is a residue of a small molecule purine or pyrimidine base;
(a) is an integer having a value of one or two, inclusive;
(b) is an integer having a value of zero or one;
X is a linker when present;
POLY is a water-soluble, non-peptidic oligomer having an end capping group selected from hydroxyl and carbon-containing end-capping groups.

In another embodiment, a compound is provided comprising a residue of a nucleoside phosphate covalently attached, either directly or through one or more atoms, to a water-soluble, non-peptidic oligomer having an end-capping group selected from hydroxyl and carbon-containing end-capping groups, having the following structure:

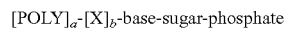

wherein:
base is a residue of a small molecule purine or pyrimidine base;
(a) is an integer having a value of one or two, inclusive;
(b) is an integer having a value of zero or one;
X is a linker when present;
POLY is a water-soluble, non-peptidic oligomer having an end capping group selected from hydroxyl and carbon-containing end-capping groups.

In one or more embodiments, a compound is provided, the compound having the following structure:

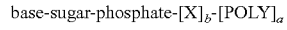

wherein:
base is a residue of a small molecule purine or pyrimidine base;
(a) is an integer having a value of one or two, inclusive;
(b) is an integer having a value of zero or one;
X is a linker when present and in each occurrence;
POLY is a water-soluble, non-peptidic oligomer having an end capping group selected from hydroxyl and carbon-containing end-capping groups.

In one or more embodiments, a compound is provided, the compound having the following structure:

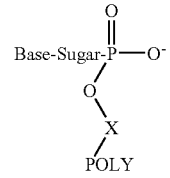

wherein:
base is a residue of a small molecule purine or pyrimidine base;
(a) is an integer having a value of one or two, inclusive;
(b) is an integer having a value of zero or one;
X is a linker when present; and
POLY is a water-soluble, non-peptidic oligomer having an end capping group selected from hydroxyl and carbon-containing end-capping groups.

In one or more embodiments, a compound is provided, the compound having the following structure:

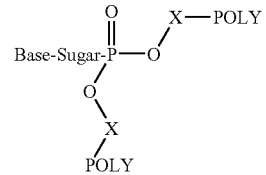

wherein:
base is a residue of a small molecule purine or pyrimidine base;
(a) is an integer having a value of one or two, inclusive;
(b) is an integer having a value of zero or one;
X is a linker when present; and
POLY is a water-soluble, non-peptidic oligomer having an end capping group selected from hydroxyl and carbon-containing end-capping groups.

In one or more embodiments, a compound is provided, the compound having the following structure:

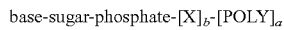

wherein:
base is a residue of a small molecule purine or pyrimidine base;
(a) is an integer having a value of one or two, inclusive;
(b) is an integer having a value of zero or one;
X is a linker when present; and
POLY, is a water-soluble, non-peptidic oligomer having an end capping group selected from hydroxyl and carbon-containing end-capping groups; with a proviso that the base or the sugar is non-naturally occurring.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is selected from the group consisting of N-glycosides of 5-fluorouracil and salts thereof with medicinally acceptable bases. These and other compounds may be synthesized using the processes known to one skilled in the art and are also disclosed in U.S. Pat. No. 2,885,396.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is selected from the group consisting of 5-fluorouracil nucleotides and salts thereof with pharmaceutically acceptable bases. These and other compounds may be synthesized using the processes known to one skilled in the art and are also disclosed in U.S. Pat. No. 2,970,139.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is 1-(3',5'-diaroyl-2'-deoxy-D-ribofuranosyl)-5-fluorouracil.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is selected from the group consisting of 1-(3',5'-di[p-chlorobenzoyl]-2'-deoxy-D-ribofuranosyl)-5-fluorouracil, 1-(3',5'-di[p-toluoyl]-2'-deoxy-D-ribofuranosyl)-5-fluorouracil, and 1-(3',5'-di[p-toluoyl]-2'-deoxy-D-ribofuranosyl)-thymine. These and other compounds may be synthesized using the processes known to one skilled in the art and are also disclosed in U.S. Pat. No. 2,949,451.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is 5-fluorouracil and salts thereof. These and other compounds may be synthesized using the processes known to one skilled in the art and are also disclosed in U.S. Pat. No. 2,802,005.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is mono(5-fluorouracilyl) mercury or bis(1-acetyl-5-fluorouracilyl) mercury. These and other compounds may be synthesized using the processes known to one skilled in the art and are also disclosed in U.S. Pat. No. 3,041,335.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside has a structure encompassed by the following formula:

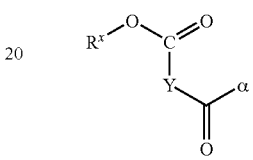

Formula I wherein $R^x$ is a pyridyl group optionally having 1 to 4 substituents selected from the group consisting of hydroxy group, oxo group, halogen atom, amino group, carboxyl group, cyano group, nitro group, carbamoyl group, lower alkylcarbamoyl group, carboxy-lower alkylcarbamoyl group, lower alkoxycarbonyl-lower alkylcarbamoyl group, phenylcarbamoyl optionally substituted with 1 to 3 substituents selected from the group consisting of halogen atom, lower alkoxy group and lower alkyl group on the phenyl ring, lower alkyl group, lower alkenyl group, lower alkoxycarbonyl group, tetrahydrofuranyl group, tetrahydropyranyl group, lower alkoxylower alkyl group, lower alkylthio-lower alkyl group, phenyl-lower alkoxy-lower alkyl group, phthalidyl group and acyloxy group, and Y is an arylene group selected from the group consisting of phenylene, naphthalene, pyridinediyl, pyrazinediyl, furandiyl and 4-pyridon-1-lower alkyl-diyl; and wherein the acyl moiety of the acyloxy group is selected from the group consisting of:
(i) $C_1$-$C_{20}$ alkenoyl groups optionally substituted with a substituent selected from the group consisting of halogen atom, hydroxy group, lower alkoxy group, aryloxy group, substituted or unsubstituted aryl group, phenyl-lower alkoxycarbonyl group and lower alkylcarbamoyl group,
(ii) arylcarbonyl groups optionally substituted with lower alkylenedioxy group or with 1 to 3 substituents selected from the group consisting of halogen atom, lower alkyl group, lower alkoxy group, carboxy group, lower alkoxycarbonyl group, nitro group, cyano group, phenyl-lower alkoxycarbonyl group, hydroxy group, guanidyl group, phenyl-lower alkoxy group, amino group and amino group substituted with lower alkyl group,
(iii) thienylcarbonyl, furanylcarbonyl, thiazolylcarbonyl, quinolylcarbonyl, pyrazinylcarbonyl, pyridylcarbonyl,
(iv) aryloxycarbonyl groups or straight or branched-chain or cyclic alkoxycarbonyl groups,
(v) ($C_3$-$C_8$ cycloalkyl) carbonyl groups optionally substituted with halogen, hydroxy, lower alkoxy or lower alkyl,
(vi) lower alkenyl or lower alkynyl carbonyl groups, and
(vii) lower alkenyl or lower alkynyl oxycarbonyl groups;
and α is a group which is formed from a 5-fluorouracil derivative linked by an amide linkage to the carbonyl group to which it is attached, and which is represented by the formula

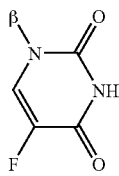

wherein β represents hydrogen atom, tetrahydrofuranyl, lower alkylcarbamoyl, phthalidyl, lower alkoxy-lower alkyl or lower alkanoyloxy-lower alkoxycarbonyl group.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is 3-[3-(6-benzoyloxy-3-cyano-2-pyridyloxycarbonyl)benzoyl]-1-ethoxymethyl-5-fluorouracil. These and other compounds may be synthesized using the processes known to one skilled in the art and are also disclosed in U.S. Pat. No. 4,983,609.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside has a structure encompassed by the following formula:

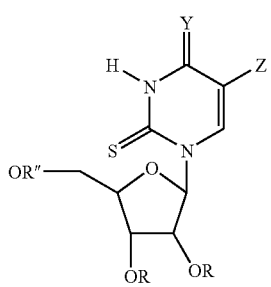

Formula II wherein R is hydrogen, or an acyl radical of the formula $R^2CO$ where R2 is lower alkyl, phenyl or substituted phenyl groups;
R" is hydrogen;
R' where R' is acyl as defined above or methyl substituted by one or more phenyl or substituted phenyl groups;
Y is OH, SH, $NH_2$, $NR^3R^4$ where $R^3$ and $R^4$ are each hydrogen or lower alkyl or NHOH; and
Z is hydrogen, halogen, lower alkyl, halogenated lower alkyl, or Nr3R4 where R3 and R4 are each hydrogen or lower alkyl.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is 2,2'-Anhydro-(1-β-D-arabinofuranosyl)cytosine. These and other compounds may be synthesized using the processes known to one skilled in the art and are also disclosed in U.S. Pat. No. 3,463,850.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside has a structure encompassed by the formula:

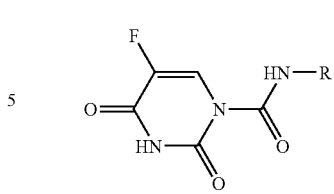

Formula III wherein R represents alkyl.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is 5-fluoro-1-hexylcarbamoyluracil. These and other compounds may be synthesized using the processes known to one skilled in the art and are also disclosed in U.S. Pat. No. 4,071,519.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is azacitidine. These and other compounds may be synthesized using the processes known to one skilled in the art and are also disclosed in U.S. Pat. No. 3,350,388.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside has a structure encompassed by the following formula:

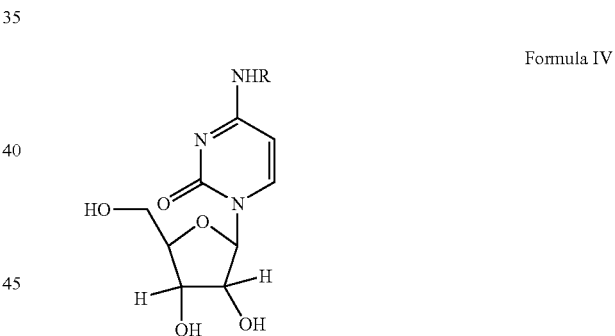

Formula IV wherein R is an aliphatic acyl group having 14 to 35 carbon atoms.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is N-(1-β-D-Arabinofuranosyl-1,2-dihydro-2-oxo-4-pyrimidinyl)docasanamide. These and other compounds may be synthesized using the processes known to one skilled in the art and are also disclosed in U.S. Pat. No. 3,991,045.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is a fully acylated 4-thiouracil-1-nucleoside and has a structure encompassed by the following formula:

Formula V

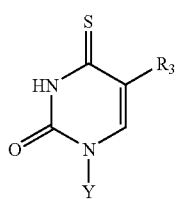

wherein R₃ is selected from the group consisting of hydrogen, alkyl containing from 1 to 8 carbon atoms, inclusive, alkenyl containing from 3 to 8 carbon atoms, inclusive, cycloalkyl containing from 4 to 8 carbon atoms, inclusive, cycloalkenyl containing from 4 to 8 carbon atoms, inclusive, aryl containing from 6 to 10 carbon atoms, inclusive, aralkyl containing from 7 to 10 carbon atoms, inclusive, hydroxyl and nitro; and Y is a sugar radical containing from 5 to 6 carbon atoms, and wherein the acyl groups are the acyl radicals of monocarboxylic acids and containing from 2 to 12 carbon atoms, inclusive, and halo-, nitro-, hydroxyl-, amino-, cyano-, thiocyano-, and lower-alkoxy-substituted hydrocarbon monocarboxylic acids containing from 2 to 12 carbon atoms, inclusive.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is 4-Amino-1-β-D-arabinofuranosyl-2(1H)-pyrimidinone. These and other compounds may be synthesized using the processes known to one skilled in the art and are also disclosed in U.S. Pat. No. 3,116,282.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside has a structure encompassed by the following formula:

Formula VI

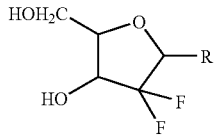

wherein R is a base selected from the group consisting of

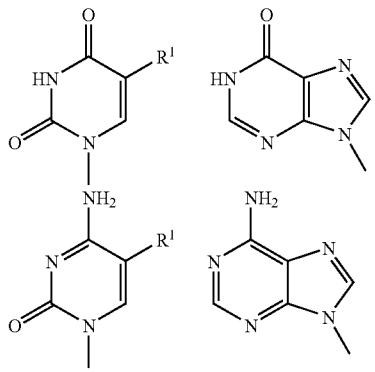

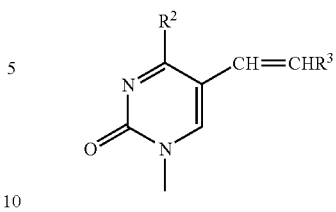

wherein

R¹ is hydrogen, methyl, bromo, fluoro, chloro or iodo;

R² is hydroxyl;

R³ is hydrogen, bromo, chloro or iodo.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is 4-amino-1-[3,3-difluoro-4-hydroxy-5-(hydroxymethyl)tetrahydrofuran-2-yl]-1H-pyrimidin-2-one. These and other compounds may be synthesized using the processes known to one skilled in the art and are also disclosed in U.S. Pat. No. 4,808,614.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside has a structure encompassed by the following formula:

Formula VII

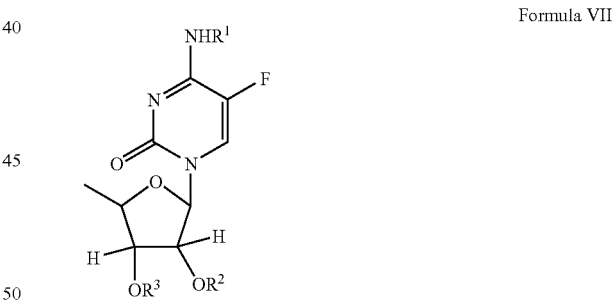

wherein R¹, R² and R³ are each independently hydrogen, or an easily hydrolyzable radical under physiological conditions, with the proviso that, at least one of R¹, R² and R³ is an easily hydrolyzable radical under physiological conditions;

as well as hydrates or solvates of the compounds of the general formula.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside has a structure encompassed by the following formula:

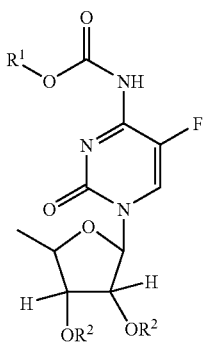

Formula VIII wherein R¹ is a saturated straight or branched hydrocarbon radical wherein the number of carbon atoms in the longest straight chain of this hydrocarbon radical ranges from three to seven, or is a radical of the formula —$(CH_2)n-^y$ wherein Y is a cyclohexyl radical, a $C_1$-$C_4$ alkoxy radical or a phenyl radical and wherein when Y is a cyclohexyl radical n is an integer from 0 to 4, and when Y is $C_1$-$C_4$ alkoxy radical or a phenyl radical n is an integer from 2 to 4, and R² is a hydrogen atom or a radical easily hydrolyzable under physiological conditions, or a hydrate or solvate thereof.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is 5'-Deoxy-5-fluoro-N-[(pentyloxy)carbonyl]cytidine. These and other compounds may be synthesized using the processes known to one skilled in the art and are also disclosed in U.S. Pat. Nos. 4,966,891 and 5,472,949.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside has a structure encompassed by the following formula:

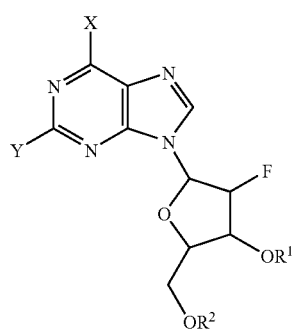

Formula IX wherein X and Y are the same or different and are hydrogen, halogen, $OR^3$, $SR^3$, $NR^3R^4$ or NHacyl; $R^3$ and $R^4$ being the same or different and being hydrogen, a lower alkyl of 1 to 7 carbon atoms, an aralkyl compound selected from the group consisting of benzyl, benzhydryl or methoxybenzyl, or an aryl compound selected from the group consisting of phenyl, chlorophenyl, toluoyl, methoxyphenyl and naphthyl; and NHacyl being alkanoyl or aroyl amide, alkanoyl being an alkyl carbonyl radical in which alkyl is a straight or branched chain saturated or unsaturated hydrocarbon radical having from 1 to 20 carbon atoms; and wherein $R^1$ and R2 are the same or different and are acyl or aroyl, acyl being an alkanoyl group of 1 to 20 carbon atoms and aroyl being benzoyl or naphthoyl.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside has a structure encompassed by the following formula:

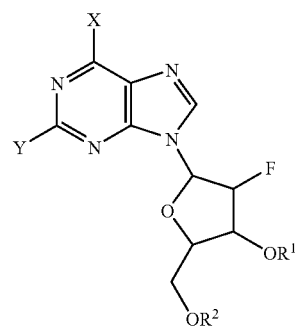

Formula X wherein X and Y are the same or different and are hydrogen, halogen, $OR^3$, $SR^3$, $NR^3R^4$ or NHacyl;
$R^3$ and $R^4$ being the same or different and being hydrogen, a lower alkyl of 1 to 7 carbon atoms, an aralkyl compound selected from the group consisting of benzyl, benzhydryl or methoxybenzyl, or an aryl compound selected from the group consisting of phenyl, chlorophenyl, toluoyl, methoxyphenyl and naphthyl; and
NHacyl being alkanoyl or aroyl amide, alkanoyl being an alkyl carbonyl radical in which alkyl is a straight or branched chain saturated or unsaturated hydrocarbon radical having from 1 to 20 carbon atoms and aroyl being a benzoyl or naphthoyl; and
wherein $R^1$ and $R^2$ are the same or different and are hydrogen, acyl or aroyl, acyl being an alkanoyl group of 1 to 20 carbon atoms and aroyl being a benzoyl or naphthoyl.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside has a structure encompassed by the following formula:

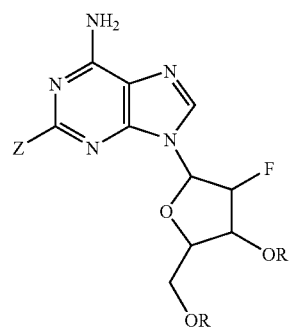

Formula XI wherein R, each which may be the same or different, is hydrogen or a protecting group;
wherein Z is a halogen of the group F, Cl, and Br; and pharmaceutically acceptable salts thereof, said composition being in combination with a pharmaceutically acceptable carrier for oral, topical, or parenteral administration.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is 5-(6-amino-2-chloro-purin-9-yl)-4-fluoro-2-(hydroxymethyl)oxolan-3-ol. These and other compounds may be synthesized using the processes known to one skilled in the art and are also disclosed in U.S. Pat. Nos. 4,751,221, 4,918,179, and 5,384,310.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is 9-(5-O-formyl-β-D-arabinofuranosyl)-2-fluoroadenine. These and other compounds may be synthesized using the processes known to one skilled in the art and are also disclosed in U.S. Pat. No. 4,357,324.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside has a structure encompassed by the following formula:

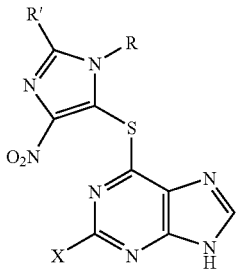

Formula XII wherein X is selected from the class consisting of hydrogen and amino, R is selected from the class consisting of methyl, benzyl, p-nitrobenzyl and hydrogen and R' is selected from the class consisting of hydrogen and the methyl group.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is 6-[(1-methyl-4-nitro-1H-imidazoyl-5-yl)thio]-1H-purin-2-amine. These and other compounds may be synthesized using the processes known to one skilled in the art and are also disclosed in U.S. Pat. No. 3,056,785.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is 2β-D-ribofuranosyl-4-thiazolecarboxamide. These and other compounds may be synthesized using the processes known to one skilled in the art and are also disclosed in Anticancer Res. 16, 3307-3354 (1996).

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is selected from the group consisting of 6-mercaptopurine, 6-purinyl disulfide, 2-amino-6-mercaptopurine, 6-thiocyanopurine, 2-amino-6-thiocyanopurine, 2-amino-6-iodopurine, 4,5-diamino. These and other compounds may be synthesized using the processes known to one skilled in the art and are also disclosed in U.S. Pat. Nos. 2,697,709, 2,800,473, 2,884,667, 3,019,224, 3,132,144, and 2,721,866.

In one or more embodiment of the invention, a compound is provided, the compound comprising a residue of a nucleoside phosphate covalently attached via a linker to a water-soluble, non-peptidic oligomer, wherein the nucleoside phosphate or the nucleoside is (R)-3-(2-deoxy-β-D-erythro-pentofuranosyl)-3,6,7,8-tetrahydroimidazo[4,5-d][1,3]diazepin-8-ol. These and other compounds may be synthesized using the processes known to one skilled in the art and are also disclosed in U.S. Pat. No. 3,923,785.

These and other compounds may be synthesized using the processes known to one skilled in the art and are also disclosed in U.S. Pat. No. 3,463,850.

Examples of specific nucleoside phosphate or the nucleosides include, but are not limited to, ancitabine, azacitidine, 6-azauridine, capacitabine, carmofur, cytarabine, decitabine, doxifluridine, emitefur, enocitabine, floxuridine, fluorouracil, gemcitabine, tegafur, cladribine, clofarabine, fludarabine, 6-mercaptopurine, pentostatin, thiamiprine, thioguanine, tiazofurin.

In one or more embodiment of the invention, a compound is provided, the compound comprising a residue of a nucleoside phosphate covalently attached via a linker to a water-soluble, non-peptidic oligomer, wherein the compound is selected from the group consisting of adenosine phosphate, guanosine phosphate, uridine phosphate, 5-methyluridine phosphate, thymidine phosphate, cytidine phosphate, deoxyadenosine phosphate, deoxyguanosine phosphate, deoxyuridine phosphate, deoxy-5-methyluridine phosphate, deoxythymidine phosphate, deoxycytidine phosphate, xanthosine phosphate, deoxyxanthosine phosphate, pseudouridine phosphate, deoxypseudouridine phosphate, orotidine phosphate, deoxyorotidine phosphate, inosine phosphate, deoxyinosine phosphate, nicatinamide adenine dinucleotide, flavin adenine dinucleotide, falvin mononucleotide, nicotinamide mononucleotide, nicotinamide adenine dinucleotide phosphate.

It is believed that an advantage of the conjugates of the present invention is their ability to retain some degree of nucleoside phosphate activity while also exhibiting a decrease in metabolism. Although not wishing to be bound by theory, it is believed that the oligomer-containing conjugates described herein, in contrast to the unconjugated "original" nucleoside phosphate, are not metabolized as readily because the oligomer serves to reduce the overall affinity of the compound to substrates that may metabolize nucleoside phosphates. In addition (and again, not wishing to be bound by theory), the extra size introduced by the oligomer, in contrast to the unconjugated "original" nucleoside phosphate, reduces the ability of the compound to cross the blood-brain barrier. Even should the linkage between the residue of the nucleoside phosphate and the oligomer be degradable, the compound still offers advantages (such as avoiding first-pass metabolism upon initial absorption).

Use of discrete oligomers (e.g., from a monodisperse or bimodal composition of oligomers, in contrast to relatively impure compositions) to form conjugates may advantageously alter certain properties associated with the corresponding small molecule drug. For instance, a conjugate of the invention, when administered by any of a number of suitable administration routes, such as parenteral, oral, transdermal, buccal, pulmonary, or nasal, exhibits reduced penetration across the blood-brain barrier. It is preferred that the conjugates exhibit slowed, minimal or effectively no crossing of the blood-brain barrier, while still crossing the gastrointestinal (GI) walls and into the systemic circulation if oral delivery is intended. Moreover, the conjugates of the invention maintain a degree of bioactivity as well as bioavailability in their conjugated form.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of solutes and drugs into the central nervous system.

For compounds whose degree of blood-brain barrier crossing ability is not known, the ability may be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses may be conducted, for example, by contract research organizations such as Absorption Systems, Exton, Pa.). More specifically, in the RBP model, a cannula is placed in the left carotid artery and the side branches are tied off. A physiologic buffer containing the compound (5 micromolar) is perfused at a flow rate of 10 mL/min in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., *J. Med. Chem.* 2000, 43, 3714-3717; and Kelder, J., et al., *Pharm. Res.* 1999, 16, 1514-1519.

With respect to the blood-brain barrier, the water-soluble oligomer-small molecule drug conjugate exhibits a blood-brain barrier crossing rate that is reduced as compared to the crossing rate of the small molecule drug not attached to the water-soluble oligomer. Exemplary reductions in blood-brain barrier crossing rates for the conjugates described herein include reductions of at least about 5%; at least about 10%; at least about 25%; at least about 30%; at least about 40%; at least about 50%; at least about 60%; at least about 70%; at least about 80%; or at least about 90%, when compared to the blood-brain barrier crossing rate of the small molecule drug not attached to the water-soluble oligomer. A preferred reduction in the blood-brain barrier crossing rate for a conjugate is at least about 20%.

As indicated above, the compounds of the invention include a residue of a nucleoside phosphate. Assays for determining whether a given compound may inhibit growth are described infra.

The nucleoside phosphates used in the conjugates are small molecule drugs, that is to say, pharmacologically active compounds having a molecular weight of less than about 1000 Daltons. Small molecule drugs, for the purpose of the invention, include oligopeptides, oligonucleotides, and other biomolecules having a molecular weight of less than about 1000 Daltons. Also encompassed in the term "small molecule drug" is any fragment of a peptide, protein or antibody, including native sequences and variants falling within the molecular weight range stated above. In one or more embodiments, however, it is preferred that the small molecule drug satisfies one or more of the following: not an oligopeptide; not an oligonucleotide; not an antibody; and not a fragment of any of the foregoing.

Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300.

The small molecule drug used in the invention, if chiral, may be obtained from a racemic mixture, or an optically active form, for example, a single optically active enantiomer, or any combination or ratio of enantiomers. In addition, the small molecule drug may possess one or more geometric isomers. With respect to geometric isomers, a composition may a mixture of two or more geometric isomers. A small molecule drug for use in the present invention may be in its customary active mode, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The nucleoside phosphate for coupling to a water-soluble, non-peptidic oligomer possesses a free hydroxyl, carboxyl, thio, amino group, or the like (i.e., "handle") suitable for covalent attachment to the oligomer. In addition, the nucleoside phosphate may be modified by introduction of a reactive group, preferably by conversion of one of its existing functional groups to a functional group suitable for formation of a stable covalent linkage between the oligomer and the drug. Both approaches are illustrated in the Experimental section.

The water-soluble, non-peptidic oligomer comprises one or more monomers serially attached to form a chain of monomers. The oligomer may be formed from a single monomer type (i.e., is homo-oligomeric) or two or three monomer types (i.e., is co-oligomeric). Preferably, each oligomer is a co-oligomer of two monomers or, more preferably, is a homo-oligomer.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) may have any of a number of different geometries. For example, the water-soluble, non-peptidic oligomer may be linear, branched, or forked. The water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers in series. In yet further embodiments, the oligomer (and the corresponding conjugate) possesses 21, 22, 23, 24, 25, 26, 27, 28, 29 or 30 monomers in series. Thus, for example, when the water-soluble, non-peptidic polymer includes $CH_3—(OCH_2CH_2)_n—$, "n" is an integer that may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and may fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the nucleoside phosphate (in contrast to the step-wise addition of one or more monomers to effectively "grow" the oligomer onto the nucleoside phosphate), it is preferred that the composition containing an activated form of the water-soluble, non-peptidic oligomer be monodispersed. In those instances, however, where a bimodal composition is employed, the composition will possess a bimodal distribution centering around any two of the above numbers of monomers. Ideally, the polydispersity index of each peak in the bimodal distribution, Mw/Mn, is 1.01 or less, and even more preferably, is 1.001 or less, and even more preferably is 1.0005 or less. More preferably, each peak possesses a MW/Mn value of 1.0000. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers may be purchased or prepared from commercial sources (e.g., Sigma-Aldrich, St. Louis, Mo.), or alternatively, may be chemically synthesized. Water-soluble, non-peptidic oligomers may be prepared as described in Chen Y., Baker, G. L., J. Org. Chem., 6870-6873 (1999), WO 02/098949, and U.S. Patent Application Publication 2005/0136031.

When present, the linker or linkage (through which the water-soluble, non-peptidic polymer is attached to the nucleoside phosphate) may be a single atom, such as an oxygen or a sulfur, two atoms, or a number of atoms. A linker may be linear in nature. The linkage, "X" is hydrolytically stable, and is preferably also enzymatically stable. Preferably, the linkage "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the linker "X" comprises an ether, amide, urethane, amine, thioether, urea, or a carbon-carbon bond. Functional groups such as those discussed below, are used for forming the linkages. The linkage may less preferably also comprise (or be adjacent to or flanked by) spacer groups, as described further below. Spacers are useful in instances where the bioactivity of the conjugate is significantly reduced due to the positioning of the oligomer on the parent drug.

More specifically, in selected embodiments, a linker of the invention, X, may be any of the following: "—" (i.e., a covalent bond, that may be stable or degradable, between the residue of the small molecule nucleoside phosphate and the water-soluble, non-peptidic oligomer), —O—, —NH—, —S—, —C(O)—, —C(O)O—, —OC(O)—, —CH$_2$—C(O)O—, —CH$_2$—OC(O)—, —C(O)O—CH$_2$—, —OC(O)—CH$_2$—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—C(O)—NH—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—C(O)—CH$_2$—, —CH$_2$—C(O)—NH—CH$_2$—CH$_2$—NH—, —CH$_2$—CH$_2$—NH—C(O)—, —CH$_2$—C(O)—NH—CH$_2$—CH$_2$—NH—C(O)—, —CH$_2$—CH$_2$—C(O)—NH—CH$_2$—CH$_2$—NH—C(O)—CH$_2$—, bivalent cycloalkyl group, —N(R)—, R is selected from the group consisting of hydrogen, alkyl, substituted alkyl, alkenyl, substituted alkenyl, alkynyl, substituted alkynyl, aryl and substituted aryl.

For purposes of the present invention, however, a series of atoms is not considered as a linkage when the series of atoms is immediately adjacent to an oligomer segment, and the series of atoms is but another monomer such that the proposed linkage would represent a mere extension of the oligomer chain.

The linkage "X" between the water-soluble, non-peptidic oligomer and the small molecule is formed by reaction of a functional group on a terminus of the oligomer (or one or more monomers when it is desired to "grow" the oligomer onto the nucleoside phosphate) with a corresponding functional group within the nucleoside phosphate. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer may have the following structure: $CH_3O—(CH_2—CH_2—O)_n—(CH_2)_p—C(O)H$, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4.

The terminus of the water-soluble, non-peptidic oligomer not bearing a functional group may be capped to render it unreactive. When the oligomer does includes a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Small molecule drugs for covalent attachment to an oligomer may possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g. hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the more hydrolytically stable. As mentioned above, more preferred are conjugates having a hydrolytically stable linkage between the oligomer and the drug. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e. aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, may be added, to form, for example, thioether bonds. These groups include maleimides, vinyl sulfones, vinyl pyridine, acrylates, methacrylates, and acrylamides. Other groups comprise leaving groups which may be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the nucleoside phosphate may not have a functional group suited for conjugation. In this instance, it is possible to modify the "original" nucleoside phosphate so that it does have a functional group suited for conjugation. For example, if the nucleoside phosphate has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxyamide followed by treatment with tolyene-2-sulfonyl chloride/base).

It is possible to prepare a conjugate of small molecule nucleoside phosphate bearing a carboxyl group wherein the carboxyl group-bearing small molecule nucleoside phosphate is coupled to an amino-terminated oligomeric ethylene glycol, to provide a conjugate having an amide group covalently linking the small molecule nucleoside phosphate to the oligomer. This can be performed, for example, by combining the carboxyl group-bearing small molecule nucleoside phosphate with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule nucleoside phosphate bearing a hydroxyl group wherein the hydroxyl group-bearing small molecule nucleoside phosphate is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

In another example, it is possible to prepare a conjugate of a small molecule nucleoside phosphate bearing a ketone group by first reducing the ketone group to form the corresponding hydroxyl group. Thereafter, the small molecule nucleoside phosphate now bearing a hydroxyl group can be coupled as described herein.

In still another instance, it is possible to prepare a conjugate of a small molecule nucleoside phosphate bearing an amine group. In one approach, the amine group-bearing small molecule nucleoside phosphate and an aldehyde-bearing oligomer are dissolved in a suitable buffer after which a suitable reducing agent (e.g., NaCNBH$_3$) is added. Following reduction, the result is an amine linkage formed between the amine group of the amine group-containing small molecule nucleoside phosphate and the carbonyl carbon of the aldehyde-bearing oligomer.

In another approach for preparing a conjugate of a small molecule nucleoside phosphate bearing an amine group, a carboxylic acid-bearing oligomer and the amine group-bearing small molecule nucleoside phosphate are combined, in the presence of a coupling reagent (e.g., DCC). The result is an amide linkage formed between the amine group of the amine group-containing small molecule nucleoside phosphate and the carbonyl of the carboxylic acid-bearing oligomer.

The conjugates of the invention can exhibit a reduced blood-brain barrier crossing rate. Moreover, the conjugates maintain at least about 5%, 10%, 20%, 30%, 40%, 50%, 60%, 70%, or more of the bioactivity of the unmodified parent small molecule drug.

The selection of an optimally sized oligomer can be determined as follows.

First, an oligomer obtained from a monodisperse or bimodal water soluble oligomer is conjugated to the small molecule drug. Preferably, the drug is orally bioavailable, and on its own, exhibits a blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. In one or more embodiments, the drug in conjugated form can be bioactive, and preferably, maintains a significant degree of bioactivity relative to the parent drug, i.e., greater than about 30% of the bioactivity of the parent drug, or even more preferably, greater than about 50% of the bioactivity of the parent drug.

Then, the above steps are repeated using oligomers of the same monomer type but having a different number of subunits.

For each conjugate whose ability to cross the blood-brain barrier is reduced in comparison to the non-conjugated small molecule drug, its oral bioavailability is then assessed. Based upon these results of sequential addition of increasing numbers of discrete monomers to a given small molecule at a given position or location within the small molecule, it is possible to determine the size of the oligomer effective in providing a conjugate having an optimal balance between reduction in biological membrane crossing, oral bioavailability, and bioactivity. The small size of the oligomers may make such screenings feasible, and may allow one to effectively tailor the properties of the resulting conjugate. By making small, incremental changes in oligomer size, and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, may determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) may also be used to study drug transport and bioavailability. In addition, non-in vivo methods include rodent everted gut excised tissue and Caco-2 cell monolayer tissue-culture models. These models are useful in predicting oral drug bioavailability.

The conjugates of the invention can then be evaluated for their biological activities, including but not limited to, antiviral activity, anti-neoplastic activity, anti-angiogenic activity and such. Such assays are known to one skilled in the art and are also disclosed in the experimental section herein. Further, such assays are also disclosed in the US and other foreign patents that are referenced herein and are herein incorporated by reference in their entirety.

The present invention also includes pharmaceutical preparations comprising a conjugate as provided herein in combination with a pharmaceutical excipient. Generally, the conjugate itself may be in a solid form (e.g., a precipitate), which may be combined with a suitable pharmaceutical excipient that may be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient may also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant may be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that may be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition may vary depending on a number of factors, but may optimally be a therapeutically effective dose when the composition is stored in a unit dose container. A therapeutically effective dose may be determined experimentally by repeated administration of increasing amounts of the conjugate in order to determine which amount produces a clinically desired endpoint.

The amount of any individual excipient in the composition may vary depending on the activity of the excipient and particular needs of the composition. The optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

The excipient may be present in the composition in an amount of about 1% to about 99% by weight, preferably from about 5%-98% by weight, more preferably from about 15-95% by weight of the excipient, with concentrations less than 30% by weight more preferred.

These foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical compositions may take any number of forms and the invention is not limited in this regard. Exemplary preparations are more preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and may also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, may be manufactured using standard tablet processing procedures and equipment. Direct compression and granulation techniques are preferred when preparing tablets or caplets containing the conjugates described herein. In addition to the conjugate, the tablets and caplets may generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition may be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (as a lyophilizate or precipitate, which may be in the form of a powder or cake), as well as formulations prepared for injection, which are liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration may take the form of nonaqueous solutions, suspensions, or emulsions, each being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein may also contain adjuvants such as preserving, wetting, emulsifying, and dispersing agents. The formulations are rendered sterile by incorporation of a sterilizing agent, filtration through a bacteria-retaining filter, irradiation, or heat.

The conjugate may also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure may contain a single or multiple reservoirs.

The conjugate may also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories may be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method may be used to treat any condition that may be remedied or prevented by administration of the particular conjugate. Those of ordinary skill in the art appreciate which conditions a specific conjugate may effectively treat. The actual dose to be administered may vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount may range from about 0.001 mg to 1000 mg, preferably in doses from 0.01 mg/day to 750 mg/day, and more preferably in doses from 0.10 mg/day to 500 mg/day.

The unit dosage of any given conjugate may be administered in a variety of dosing schedules depending on the judgment of the clinician, needs of the patient, and so forth. The specific dosing schedule may be known by those of ordinary skill in the art or may be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that a reduction in first pass metabolism may be achieved relative to the parent drug. Such a result is advantageous for many orally administered drugs that are substantially metabolized by passage through the gut. In this way, clearance of the conjugate can be modulated by selecting the oligomer molecular size, linkage, and position of covalent attachment providing the desired clearance properties. One of ordinary skill in the art can determine the ideal molecular size of the oligomer based upon the teachings herein. Preferred reductions in first pass metabolism for a conjugate as compared to the corresponding nonconjugated small drug molecule include: at least about 10%, at least about 20%, at least about 30; at least about 40; at least about 50%; at least about 60%, at least about 70%, at least about 80% and at least about 90%.

Thus, the invention provides a method for reducing the metabolism of an active agent. The method comprises the steps of: providing monodisperse or bimodal conjugates, each conjugate comprised of a moiety derived from a small molecule drug covalently attached by a stable linkage to a water-soluble oligomer, wherein said conjugate exhibits a reduced rate of metabolism as compared to the rate of metabolism of the small molecule drug not attached to the water-soluble oligomer; and administering the conjugate to a patient. Typically, administration is carried out via one type of administration selected from the group consisting of oral administration, transdermal administration, buccal administration, transmucosal administration, vaginal administration, rectal administration, parenteral administration, and pulmonary administration.

All articles, books, patents, patent publications and other publications referenced herein are incorporated by reference in their entireties.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031.

$^1$H NMR (nuclear magnetic resonance) data was generated by a 300 MHz NMR spectrometer manufactured by Bruker.

EXAMPLE 1

Synthesis of mPEG$_n$-5'-Floxuridine Monophosphate Conjugates

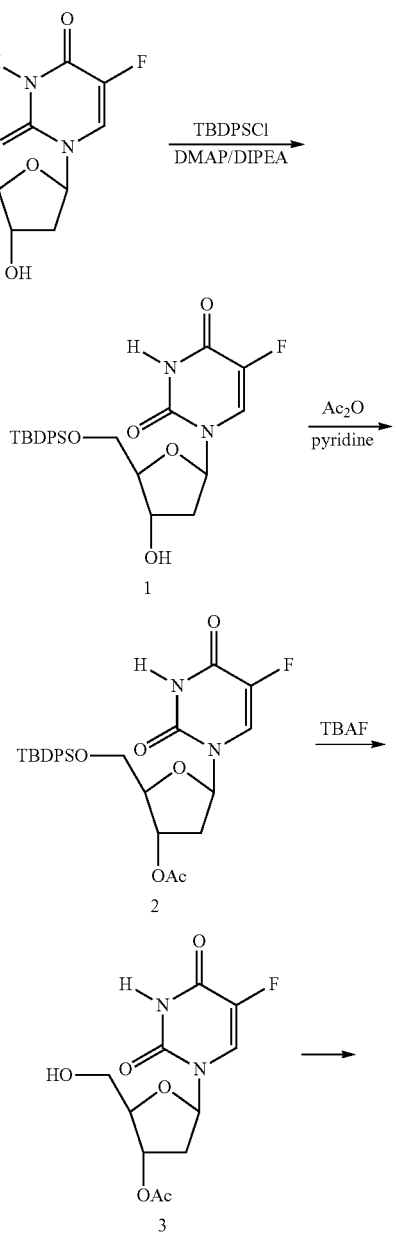

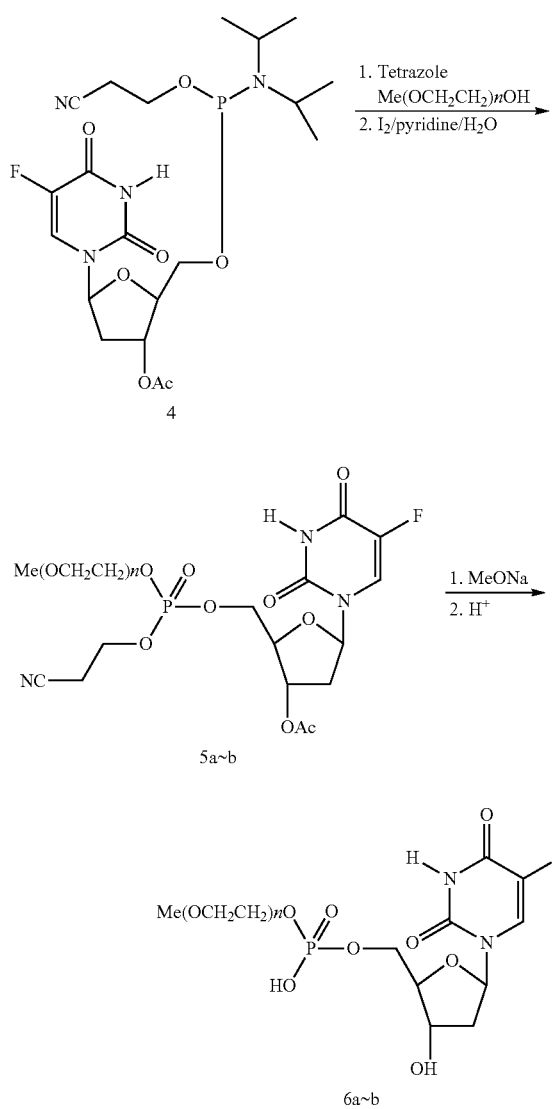

a, n = 3
b, n = 7

5'-O-TBDPS-floxuridine (1): Floxuridine (3.0 g, 12.2 mmol), DMAP (1.37 g), and DIPEA (4.8 ml) were dissolved in anhydrous DMF (30 ml). TBDPSCl (3.15 ml) was added into the solution slowly at room temperature. The reaction solution was allowed to stir overnight. Methanol (5 ml) was added. After 5 minutes, the solvent was evaporated under reduced pressure. The resulting residue was subjected to flash chromatography (MeOH/DCM=2%~7%) to give the desired compound, 1 (4.9 g, 10.1 mmol, 83%). $^1$HNMR (DMSO-$d_6$): δ 7.89 (d, 1H), 7.65-7.62 (m, 4H), 7.50-7.42 (m, 6H), 6.15 (t, 1H), 5.34 (d, 1H), 4.29-4.26 (m, 1H), 3.90-3.85 (m, 2H), 3.77-3.73 (m, 1H), 2.20-2.16 (m, 2H), 1.01 (s, 9H).

3'-O-Ac-5'-O-TBDPS-floxuridine (2): 5'-O-TBDPS-floxuridine 1 (3.5 g, 7.2 mmol) was dissolved in pyridine (8.1 ml, 100 mmol). Acetic anhydride (2.9 ml, 30 mmol)) was added slowly at room temperature. The reaction solution was allowed to stir overnight. The reaction was worked up by washing with sat. NaHCO$_3$ solution (50 ml). The mixed solution was extracted with DCM (50 ml×3). The organic phases were combined and dried with anhydrous Na$_2$SO$_4$. After filtering off the solid, the solvent was removed under reduced pressure to give compound 2 (3.5 g, 6.7 mmol, yield 92%), which was pure by TLC and used directly for next step.

3'-O-Ac-floxuridine (3): 3'-O-Ac-5'-O-TBDPS-floxuridine 2 (3.5 g, 6.7 mmol) was dissolved in THF (30 ml). At room temperature, Bu$_4$NF (15 ml, 1.0 M in THF, 15 mmol) was added into the solution. The reaction solution was stirred at room temperature for 3 hrs. The solvent was removed under reduced pressure. The resulting residue was subjected to flash chromatography (CH$_3$OH/CH$_2$Cl$_2$=2%~10%) to obtain compound 3 (1.8 g, 6.2 mmol, yield 93%). $^1$HNMR (DMSO-$d_6$): δ 11.86 (s, 1H), 8.21 (d, 1H), 6.18-6.14 (m, 1H), 5.33-5.30 (m, 1H), 5.22-5.21 (m, 1H), 4.02-4.01 (m, 1H), 3.66-3.63 (m, 2H), 2.29-2.27 (m, 2H), 2.06 (s, 3H).

3'-O-Ac-5'-(2-Cyanoethyl diisopropylphosphoramidite)-floxuridine (4): 3'-O-Ac-floxuridine 3 (1.09 g, 4.0 mmol) and DIPEA (1.33 ml, 8 mmol) were dissolved in anhydrous DCM (50 ml). At room temperature, 2-cyanoethyl diisopropylchlorophosphoramidite (1.15 ml, 5.0 mmol) was added to the solution dropwise. The solution was stirred for 30 minutes at room temperature and then washed with sat. NaHCO$_3$ solution (25 ml). The mixed solution was extracted with DCM (25 ml×3). The organic phases were combined and dried with anhydrous Na$_2$SO$_4$. After filtering off solid, the solvent was removed under reduced pressure and the residue (2.4 g) was used directly for next step without further purification.

2-Cyanoethyl 5'-(2'-O-Ac-floxuridine) methoxy tri(ethylene glycol) phosphate (5a): Intermediate 4 (2.4 g) and tri(ethylene glycol) monomethyl ether (787 mg, 4.8 mmol) were dissolved in anhydrous acetonitrile (50 ml). At room temperature, tetrazole solution (10.7 ml, 0.45 M in acetonitrile, 4.8 mmol) was added into the reaction solution. The reaction solution was then stirred at room temperature for 4 hours. Iodine solution (110 ml, 0.1 M in THF/pyridine/H$_2$O 78:20:2) was added. After 10 minutes, Na$_2$S$_2$O$_3$ solution (5 g in 200 ml H$_2$O) was added. After 5 minutes, the mixed solution was extracted with DCM (100 ml×3). The organic phase were combined and dried with anhydrous Na$_2$SO$_4$. After filtering off solid, the solvent was removed under reduced pressure and the resulting residue was subjected to flash chromatography (Acetone/EtOAc=10%~70%) to obtain compound 5a (1.1 g, 1.9 mmol, yield for two steps, 48%). $^1$HNMR (CDCl$_3$): δ 8.44 (s, 1H), 7.84 (d, 1H), 6.35-6.31 (m, 1H), 5.35-5.32 (m, 1H), 4.44-4.34 (m, 7H), 3.74-3.39 (m, 10H), 3.39 (s, 3H), 2.82 (t, 3H), 2.80-2.70 (m, 1H), 2.24-2.14 (m, 1H), 2.13 (s, 3H).

2-Cyanoethyl 5'-(2'-O-Ac-floxuridine) methoxy hepta(ethylene glycol) phosphate (5b): Intermediate 4 (2.4 g) and hepta(ethylene glycol) monomethyl ether (1.63 g, 4.8 mmol) were dissolved in anhydrous acetonitrile (50 ml). At room temperature, tetrazole solution (10.7 ml, 0.45 M in acetonitrile, 4.8 mmol) was added into the reaction solution. The reaction solution was then stirred at room temperature for 4 hours. Iodine solution (110 ml, 0.1 M in THF/pyridine/H$_2$O 78:20:2) was added. After 10 minutes, Na$_2$S$_2$O$_3$ solution (5 g in 200 ml H$_2$O) was added. After 5 minutes, the mixed solution was extracted with DCM (100 ml×3). The organic phases were combined and dried with anhydrous Na$_2$SO$_4$. After filtering off solid, the solvent was removed under reduced pressure and the resulting residue was subjected to flash chromatography (Acetone/EtOAc=30%~90%) to obtain compound 5b (1.3 g, 1.7 mmol, yield for two steps 43%). $^1$HNMR (CDCl$_3$): δ 7.78 (d, 1H), 6.32-6.27 (m, 1H), 5.31-5.29 (m, 1H), 4.39-4.19 (m, 7H), 3.70-3.51 (m, 26H), 3.36 (s, 3H), 2.82 (t, 3H), 2.80-2.70 (m, 1H), 2.22-2.19 (m, 1H), 2.09 (s, 3H).

5'-floxuridine methoxy tri(ethylene glycol) phosphate (6a): Compound 5a (1.1 g, 1.94 mmol) was dissolved in methanol (30 ml). At room temperature, sodium methoxide in methanol (25% wt, 2.0 ml) was added into the solution. The reaction solution was stirred for 4.5 hours at room temperature. Dowex resin (hydrogen form, 50 W×4-200, 20 g) was added and stirring continued for 10 minutes. The resin was filtered off and the solvent was removed under reduced pressure. The resulting residue was subjected to flash chromatography (MeOH/DCM=10%~80%) to give compound to give compound 6a (0.9 g, 1.90 mmol, yield 98%). $^1$HNMR (MeOD): δ 7.94 (d, 1H), 6.30-6.26 (m, 1H), 4.46-4.44 (m, 1H), 4.26-4.16 (m, 5H), 3.72-3.54 (m, 10H), 3.35 (s, 3H), 2.32-2.21 (m, 2H). LC/MS 473 [M+H]$^+$.

5'-floxuridine methoxy hepta(ethylene glycol) phosphate (6b): Compound 5b (0.8 g, 1.1 mmol) was dissolved in methanol (20 ml). At room temperature, sodium methoxide in methanol (25% wt, 1.5 ml) was added into the solution. The reaction solution was stirred for 4.5 hours at room temperature. Dowex resin (hydrogen form, 50 W×4-200, 18 g) was added and stirring was continued for 10 minutes. The resin was filtered off and the solvent was removed under reduced pressure. The resulting residue was subjected to flash chromatography (MeOH/DCM=10%~80%) to give compound 6b (0.65 g, 1.0 mmol, yield 91%). $^1$HNMR (MeOD): δ 7.99 (d, 1H), 6.29-6.27 (m, 1H), 4.47-4.46 (m, 1H), 4.22-4.09 (m, 5H), 3.71-3.59 (m, 26H), 3.37 (s, 3H), 2.29-2.23 (m, 2H). LC/MS 649 [M+H]$^+$.

EXAMPLE 2

Synthesis of mPEG$_n$-5'-Gemcitabine Monophosphate Conjugates

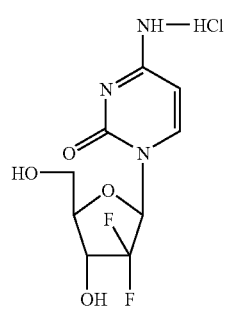

1

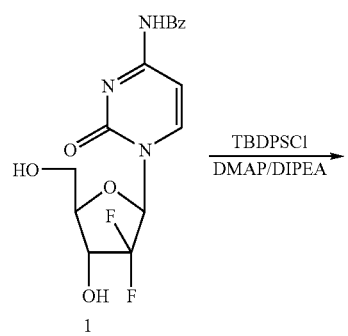

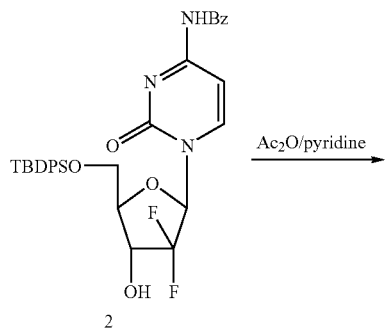

2

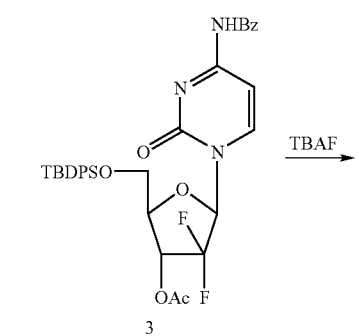

3

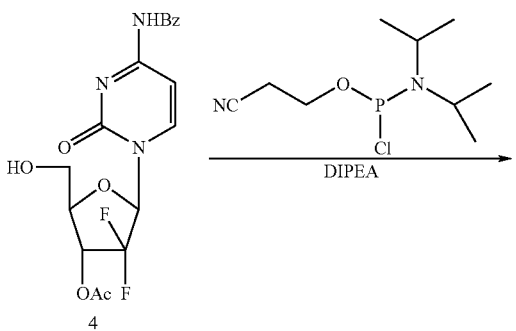

4

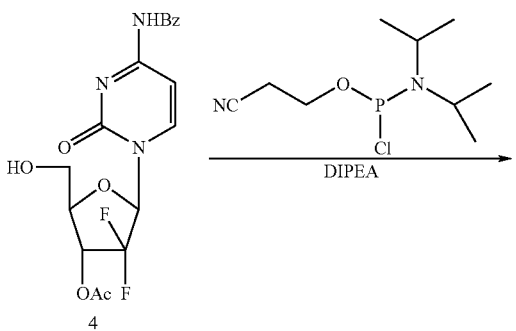

5

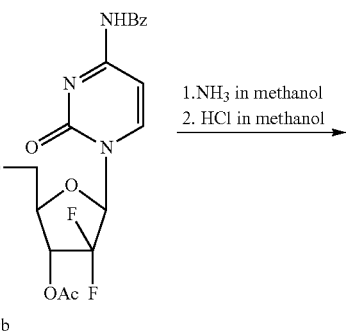

6a~b

-continued

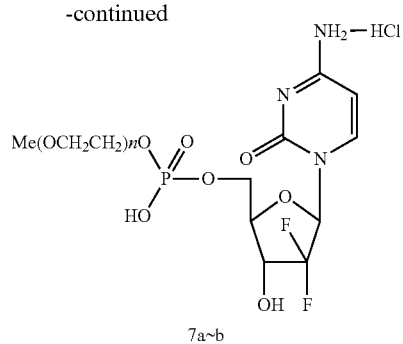

7a~b a, n = 3
b, n = 7

N-Benzoyl-gemcitabine (1): A mixture of gemcitabine hydrochloride (300 mg, 1 mmol), hexamethyldisilazane (5 ml), and a catalytic amount of ammonium sulfate (5 mg) in dioxane (5 ml) was heated under reflux for 2.5 hours. The dioxane was evaporated and the reaction mixture was dissolved in toluene (20 ml) and then evaporated three times. After removal of toluene, the residue was dissolved in dichloromethane (10 ml). To this solution was added N-methylimidazole (0.24 ml, 3 mmol) and benzoyl chloride (0.35 ml, 3 mmol) and the solution was stirred for three hours at room temperature. The reaction mixture was then concentrated to an oily residue, which was dissolved in a solution of triethylamine (3 ml) and methanol (20 ml). This solution was stirred for 1.5 hours at room temperature. The product was purified by flash chromatography ($CH_2Cl_2$/MeOH=2%~10%) to give N-benzoyl-gemcitabine 1 (303 mg, yield 83%). NMR (MeOD): δ 8.25 (d, 1H), 7.81-7.80 (m, 2H), 7.56-7.22 (m, 4H), 6.14-6.04 (m, 1H), 4.21-4.10 (m, 1H), 3.83-3.80 (m, 2H), 3.72-3.61 (m, 2H).

N-Benzoyl-5'-O-TBDPS-gemcitabine (2): N-Benzoyl-gemcitabine 1 (1.17 g, 3.2 mmol), DMAP (1 mmol), and DIPEA (0.7 ml, 4.0 mmol) were dissolved in anhydrous DMF (30 ml). TBDPSCl (1.32 ml, 5.1 mmol) was added into the solution slowly at room temperature and the solution was allowed to stir overnight. Methanol (5 ml) was added. After 5 minutes, the solvent was removed under reduced pressure. The resulting residue was subjected to flash chromatography (EtOAc/Haxanes=10%~80%) to give compound 2 (1.5 g, 2.5 mmol, yield 78%). $^1$HNMR ($CDCl_3$): δ 8.10 (d, 1H), 7.91 (d, 2H), 7.71-7.42 (m, 13H), 6.48-6.44 (m, 1H), 4.59-4.49 (m, 1H), 4.17-3.95 (m, 4H), 1.13 (s, 9H).

N-Benzoyl-3'-O-Ac-5'-O-TBDPS-gemcitabine (3): N-Benzoyl-5'-O-TBDPS-gemcitabine 2 (1.5 g, 2.5 mmol) was dissolved in pyridine (8.1 ml, 100 mmol). Acetic anhydride (5.0 ml, 50 mmol)) was added slowly at room temperature and the solution was allowed to stir overnight. The reaction was worked up by washing with sat. $NaHCO_3$ solution (50 ml). The mixed solution was extracted with DCM (50 ml×3). The organic phases were combined and dried with anhydrous $Na_2SO_4$. After filtering off solid, the solvent was removed under reduced pressure to give compound 3 (1.5 g, 2.3 mmol, yield 92%), which was pure by TLC and thus used directly for next step.

N-Benzoyl-3'-O-Ac-gemcitabine (4): N-Benzoyl-3'-O-Ac-5'-O-TBDPS-gemcitabine 3 (1.5 g, 2.3 mmol) was dissolved in THF (30 ml). At room temperature, a mixture of $Bu_4NF$ (4.0 ml, 1.0 M in THF, 4.0 mmol) and acetic acid (0.4 ml) was added into the solution. The reaction solution was stirred at room temperature for 4 hrs. The solvent was removed under reduced pressure. The residue was subjected to flash chromatography ($CH_3OH/CH_2Cl_2$=2%~10%) to obtain compound 4 (0.82 g, 2.0 mmol, yield 87%). $^1$HNMR (MeOD): δ 8.39-8.36 (d, 1H), 8.02-7.99 (m, 2H), 7.70-7.54 (m, 4H), 6.42-6.37 (m, 1H), 5.52-5.45 (m, 1H), 4.30-4.27 (m, 1H), 4.00-3.79 (m, 2H), 2.20 (s, 3H).

N-Benzoyl-3'-O-Ac-5'-(2-Cyanoethyl diisopropylphosphoramidite)-gemcitabine (5): N-benzoyl-3'-O-Ac-gemcitabine 4 (360 mg, 0.88 mmol) and DIPEA (0.25 ml, 1.5 mmol) were dissolved in anhydrous DCM (50 ml). At room temperature, 2-cyanoethyl diisopropylchlorophosphoramidite (0.28 ml, 1.2 mmol) was added to the solution dropwise. The solution was stirred at room temperature for 30 minutes and then washed with sat. $NaHCO_3$ solution (25 ml). The mixed solution was extracted with DCM (25 ml×3). The organic phases were combined and dried with anhydrous $Na_2SO_4$. After filtering off solid, the solvent was removed under reduced pressure and the resulting residue (530 mg) was used directly for next step without further purification.

2-Cyanoethyl 5'-(N-benzoyl-2'-O-Ac-gemcitabine) methoxy tri(ethylene glycol) phosphate (6a): Intermediate 5 (530 mg) and tri(ethylene glycol) monomethyl ether (164 mg, 1.0 mmol) were dissolved in anhydrous acetonitrile (10 ml). At room temperature, tetrazole solution (2.4 ml, 0.45 M in acetonitrile, 1.1 mmol) was added into the reaction solution. The reaction solution was then stirred for 4 hours at room temperature. Iodine solution (20 ml, 0.1 M in THF/pyridine/$H_2O$ 78:20:2) was added. After 10 minutes, $Na_2S_2O_3$ solution (2.5 g in 100 ml $H_2O$) was added. After 5 minutes, the mixed solution was extracted with DCM (100 ml×3). The organic phases were combined and dried with anhydrous $Na_2SO_4$. After filtering off solid, the solvent was removed under reduced pressure and the resulting residue was subjected to flash chromatography (acetone/EtOAc=10%~50%) to obtain compound 6a (280 mg, 0.41 mmol, yield for two steps, 47%). $^1$HNMR ($CDCl_3$): δ 7.95-7.87 (m, 3H), 7.58-7.53 (m, 2H), 7.48-7.43 (m, 2H), 6.45-6.40 (m, 1H), 5.40-5.35 (m, 1H), 4.42-4.26 (m, 7H), 3.63-3.50 (m, 10H), 3.30 (s, 3H), 2.80-2.76 (m, 2H), 2.15 (s, 1H).

2-Cyanoethyl 5'-(N-benzoyl-2'-O-Ac-gemcitabine) methoxy hepta(ethylene glycol) phosphate (6b): Intermediate 5 (677 mg) and hepta(ethylene glycol) monomethyl ether (463 mg, 1.3 mmol) were dissolved in anhydrous acetonitrile (15 ml). At room temperature, tetrazole solution (3.1 ml, 0.45 M in acetonitrile, 1.4 mmol) was added into the reaction solution. The reaction solution was then stirred for 4 hours at room temperature. Iodine solution (26 ml, 0.1 M in THF/pyridine/$H_2O$ 78:20:2) was added. After 10 minutes, $Na_2S_2O_3$ solution (2.5 g in 100 ml $H_2O$) was added. After 5 minutes, the mixed solution was extracted with DCM (100 ml×3). The organic phases were combined and dried with anhydrous $Na_2SO_4$. After filtering off solid, the solvent was removed under reduced pressure and the resulting residue was subjected to flash chromatography (acetone/EtOAc=10%~80%) to obtain compound 6b (610 mg, 0.7 mmol, yield for two steps 55%). $^1$HNMR ($CDCl_3$): δ 7.98-7.89 (m, 3H), 7.60-7.57 (m, 2H), 7.49-7.45 (m, 2H), 6.45-6.40 (m, 1H), 5.42-5.36 (m, 1H), 4.44-4.28 (m, 7H), 3.65-3.51 (m, 26H), 3.32 (s, 3H), 2.81-2.77 (m, 2H), 2.17 (s, 1H).

5'-gemcitabine methoxy tri(ethylene glycol) phosphate hydrochloride (7a): Compound 6a (280 mg, 0.41 mmol) was dissolved in methanol (10 ml). At room temperature, ammonia in methanol (4.5 ml, 7 N, 31.5 mmol) was added into the solution. The reaction solution was stirred at room temperature for 18 hours. The solvent was evaporated under reduced pressure. The resulting residue was dissolved in methanol (5 ml). HCl in ethyl ether (1 N, 1 ml) was then added to the solution. The solvent was removed under reduced pressure and the crude residue was subjected to flash chromatography (MeOH/DCM=10%~80%) to give compound 7a (110 mg, 0.22 mmol, yield 54%). ¹HNMR (MeOD): δ 8.02 (d, 1H), 6.26 (t, 1H), 6.16 (d, 1H), 4.35-4.01 (m, 6H), 3.71-3.54 (m, 10H), 3.38 (s, 3H). LC/MS: 490 [M+H]⁺.

5'-gemcitabine methoxy hepta(ethylene glycol) phosphate hydrochloride (7b): Compound 6b (600 mg, 0.70 mmol) was dissolved in methanol (40 ml). At room temperature, ammonia in methanol (18 ml, 7 N, 126 mmol) was added into the solution. The reaction solution was stirred at room temperature for 18 hours. The solvent was evaporated under reduced pressure. The resulting residue was dissolved in methanol (5 ml). HCl in dioxane (4 N, 0.7 ml) was then added to the solution. The solvent was removed under reduced pressure and the crude residue was subjected to flash chromatography (MeOH/DCM=10%~80%) to give compound 7b (320 mg, 0.48 mmol, yield 69%). ¹HNMR (MeOD): δ 8.07 (d, 1H), 6.33 (d, 1H), 6.22 (t, 1H), 4.44-4.19 (m, 6H), 3.69-3.56 (m, 26H), 3.38 (s, 3H). LC/MS: 666 [M+H]⁺.

EXAMPLE 3

Synthesis of Di-PEG-Floxuridine Phosphate Conjugates

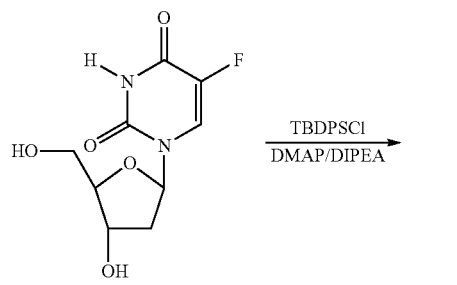

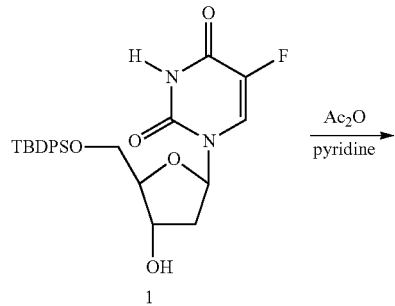

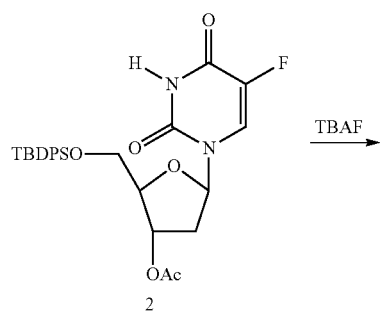

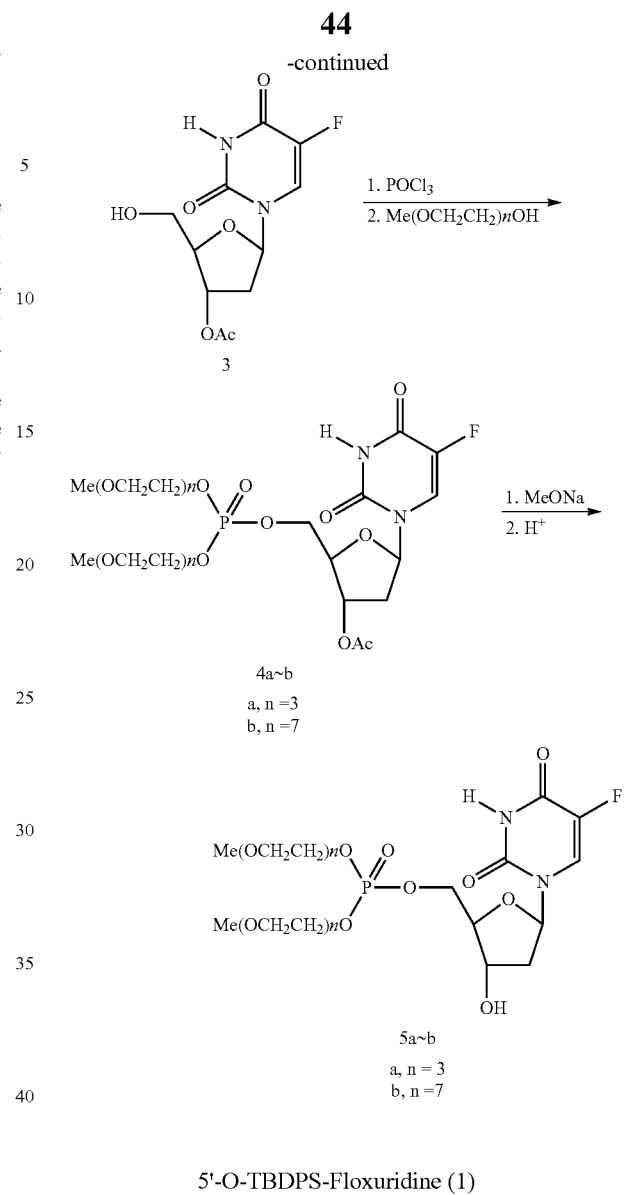

5'-O-TBDPS-Floxuridine (1)

Floxuridine (3.0 g, 12.2 mmol), DMAP (1.37 g), and DIPEA (4.8 ml) were dissolved in anhydrous DMF (30 ml). TBDPSCl (3.15 ml) was added into the solution slowly at room temperature (RT). The reaction solution was stirred at RT overnight. Methanol (5 ml) was added. After 5 minutes, the solvent was evaporated at reduced pressure. The residue was subjected to flash chromatography (MeOH/DCM=2%~7%) to obtain compound 1 (4.9 g, 10.1 mmol, 83%). ¹H NMR (DMSO-d₆): δ 7.89 (d, 1H), 7.65-7.62 (m, 4H), 7.50-7.42 (m, 6H), 6.15 (t, 1H), 5.34 (d, 1H), 4.29-4.26 (m, 1H), 3.90-3.85 (m, 2H), 3.77-3.73 (m, 1H), 2.20-2.16 (m, 2H), 1.01 (s, 9H).

3'-O-Ac-5'-O-TBDPS-Floxuridine (2)

5'-O-TBDPS-floxuridine 1 (3.5 g, 7.2 mmol) was dissolved in pyridine (8.1 ml, 100 mmol). Acetic anhydride (2.9 ml, 30 mmol)) was added slowly at RT. The reaction solution was stirred at RT overnight. The reaction was worked up by washing with sat. NaHCO₃ solution (50 ml). The mixed solution was extracted with DCM (50 ml×3). The organic phases were combined and dried with anhydrous Na₂SO₄. After filtering off the solid, the solvent was evaporated at reduced pressure to give compound 2 (3.5 g, 6.7 mmol, yield 92%), which was pure on TLC and used directly without further purification in the next step.

3'-O-Ac-Floxuridine (3)

3'-O-Ac-5'-O-TBDPS-floxuridine 2 (3.5 g, 6.7 mmol) was dissolved in THF (30 ml). At RT, Bu$_4$NF (15 ml, 1.0 M in THF, 15 mmol) was added into the solution. The reaction solution was stirred at RT for 3 hrs. The solvent was evaporated at reduced pressure. The resulting residue was subjected to flash chromatography (CH$_3$OH/CH$_2$Cl$_2$=2%~10%) to obtain compound 3 (1.8 g, 6.2 mmol, yield 93%). $^1$HNMR (DMSO-d$_6$): δ 11.86 (s, 1H), 8.21 (d, 1H), 6.18-6.14 (m, 1H), 5.33-5.30 (m, 1H), 5.22-5.21 (m, 1H), 4.02-4.01 (m, 1H), 3.66-3.63 (m, 2H), 2.29-2.27 (m, 2H), 2.06 (s, 3H).

3'-O-Ac-5'-[di-methoxy tri(ethylene glycol)phosphate]-floxuridine (4a)

3'-O-Ac-floxuridine 3 (170 mg, 0.62 mmol) was dissolved in anhydrous pyridine (3 ml). At −40° C. under N$_2$, POCl$_3$ (0.08 ml, 0.88 mmol) was added to the solution. The solution was stirred at −40° C. for 15 minutes. Tri(ethylene glycol) monomethyl ether (394 mg, 2.4 mmol) was then added to solution. The reaction solution was stirred and allowed to warm to room temperature slowly over 4 hours. The solvent was evaporated at reduced pressure. The residue was used for next step directly without further purification.

3'-O-Ac-5'-[di-methoxy hepta(ethylene glycol)phosphate]-floxuridine (4b)

3'-O-Ac-floxuridine 3 (190 mg, 0.70 mmol) was dissolved in anhydrous pyridine (3 ml). At −40° C. under N$_2$, POCl$_3$ (0.07 ml, 0.77 mmol) was added to the solution. The solution was stirred at −40° C. for 15 minutes. Hepta(ethylene glycol) monomethyl ether (850 mg, 2.5 mmol) was then added to solution. The reaction solution was stirred and allowed to warm to room temperature slowly over 4 hours. The solvent was evaporated at reduced pressure. The residue was used for next step directly without further purification.

5'-floxuridine di-methoxy tri(ethylene glycol) phosphate (5a)

Compound 4a was dissolved in methanol (10 ml). At RT, sodium methoxide in methanol (0.1 N, 14 ml) was added to the solution. The reaction solution was stirred at RT for 1 hour. Then 1.0 N HCl (1.6 ml) was added. The solvent was evaporated. The residue was subjected to flash chromatography (MeOH/DCM=2%~10%) to give compound 5a (300 mg, 0.49 mmol, yield 69%). $^1$HNMR (CDCl$_3$): δ 8.47 (m, 1H), 7.82 (d, 1H), 6.28 (t, 1H), 4.64-4.62 (m, 1H), 4.43-4.22 (m, 6H), 4.09-4.05 (m, 1H), 4.00-3.97 (m, 1H), 3.74-3.54 (m, 20H), 3.40 (s, 6H), 2.43-2.41 (m, 1H), 2.21-2.16 (m, 1H). LC/MS 619 [M+H]$^+$.

5'-floxuridine di-methoxy hepta(ethylene glycol) phosphate (5b)

Compound 4b was dissolved in methanol (10 ml). At RT, sodium methoxide in methanol (0.5 N, 4 ml) was added to the solution. The reaction solution was stirred at RT for 2 hours. Then 1.0 N HCl (2.2 ml) was added. The solvent was evaporated. The residue was subjected to flash chromatography (MeOH/DCM=3%~10%) to give compound 5a (375 mg, 0.39 mmol, yield 55%). $^1$HNMR (CDCl$_3$): δ 8.84 (m, 1H), 7.82 (d, 1H), 6.28 (t, 1H), 4.60-4.57 (m, 1H), 4.40-4.22 (m, 6H), 4.09-4.05 (m, 1H), 3.97-3.94 (m, 1H), 3.74-3.54 (m, 52H), 3.39 (s, 6H), 2.41-2.39 (m, 1H), 2.21-2.15 (m, 1H). LC/MS 971 [M+H]$^+$.

These and other compounds of the invention may be similarly synthesized using the methods described herein, as well as using techniques known to one skilled in the art.

EXAMPLE 4

The NS5B protein of hepatitis C virus (HCV) contains the RNA-dependent RNA polymerase that is the catalytic component of the HCV replication machinery. Since NS5B polymerase synthesizes RNA from an RNA template, selective molecules, shown below, have been generated to inhibit the production of viral genomic DNA. Attaching a water-soluble, non-peptidic polymer can improve these inhibitors further. The benefits of PEGylation here are: improved oral bioavailability (~4%), decreased dose (e.g. 3000 mg daily doses), reduced metabolism, and delivery of the active monophosphate form which then gets phosphorylated to the di- and tri-phosphates.

3'-valine ester of 2'-C-methylcytidine Valopicitabine (NM283)

2'-O-methylcytidine

2'-C-methyladenosine

2'-C-methylguanosine

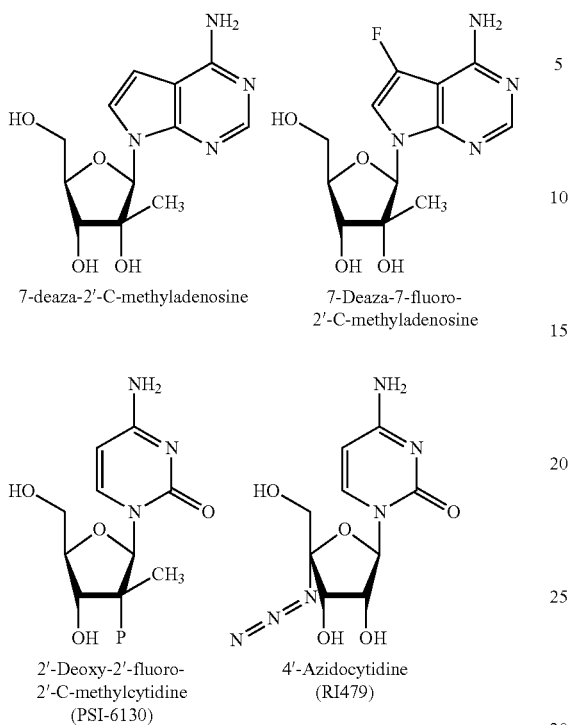
Synthesis of Pathway for PEG-NS5B Polymerase Inhibitor, PSI-6130
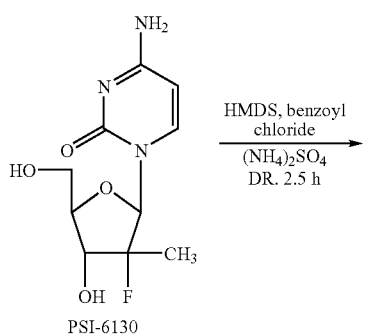
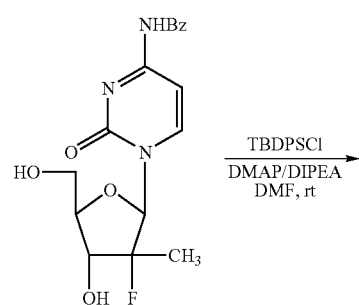
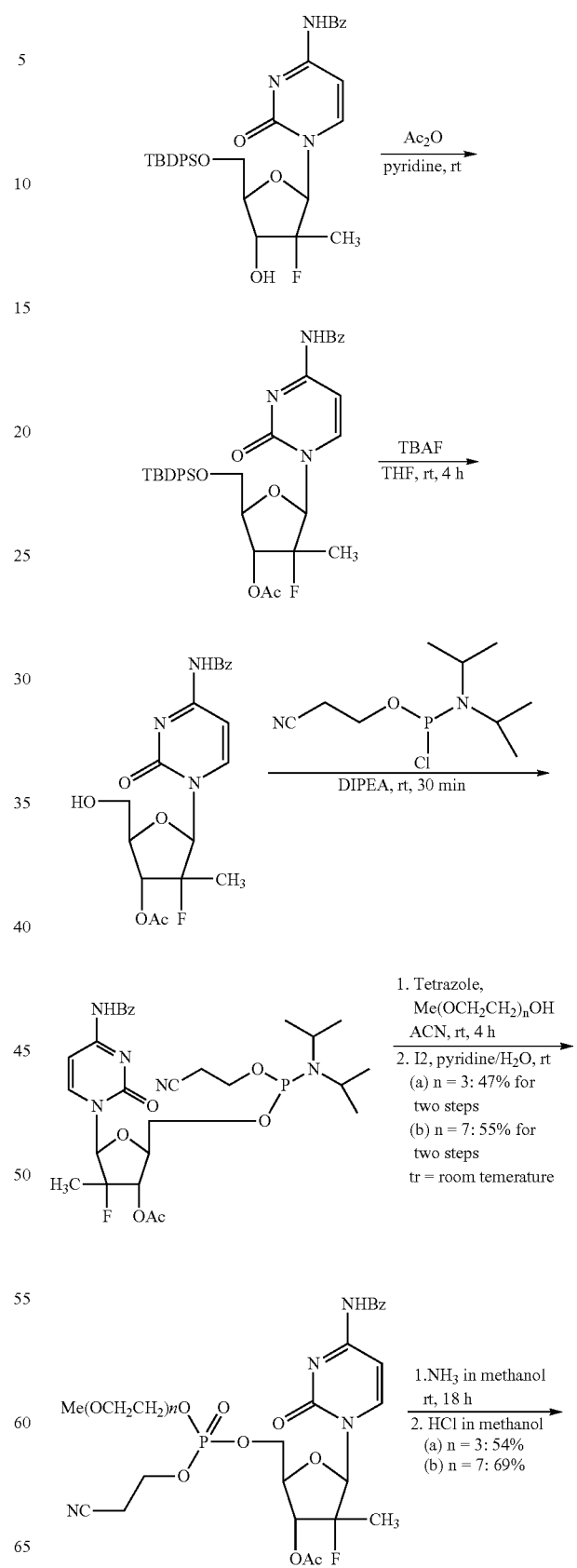

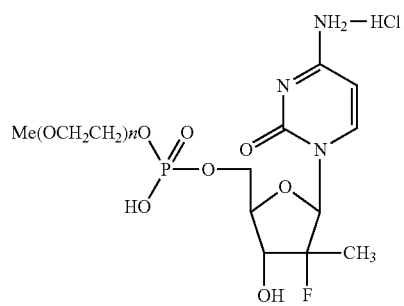

Similarly, a water-soluble, non-peptidic polymer can be attached to compounds mentioned above, and other compounds, e.g.:

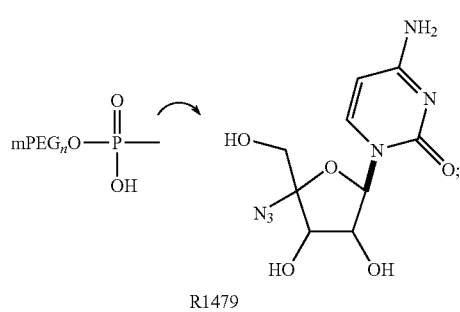

or R1626 which is a pro-drug form of R1479.

PSI-6130, as shown,

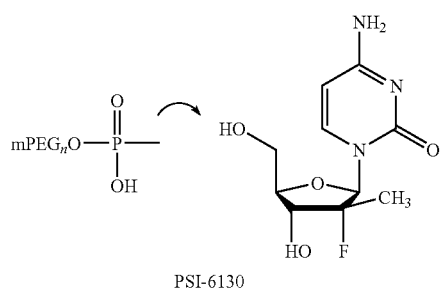

or R7128 which is a pro-drug form of PSI-6130.

Valopicitabine, shown below, is a nucleoside analogue and the orally bioavailable prodrug of NM107 that competitively inhibits the NS5B polymerase, causing chain termination.

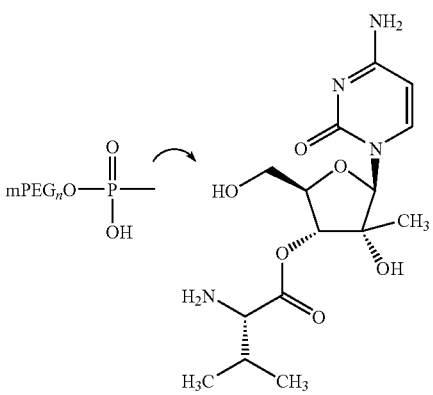

Example 5

In Vitro Screening of PEG-Floxuridine Monophosphate in Selected Human Cancer Cell Lines Experimental Design Test articles: Pegylated Floxuridines Test system: Human cancer cell lines—Colon (HT29), Ovary (A2780), Lung (HOP62), and Prostate (DU145) Breast (MCF-7).

Reference drug: Floxuridine

Dose levels: Four concentrations (10-4-10-7 Molar concentration) in triplicate.

Method: Sulforhodamine B (SRB) assay with 48 h drug exposure

Reference: *Nature Protocols* 1, 1112-1116 (2006)

Conjugates mono-mPEG$_3$-5'-Gemcitabine monophosphate
mono-mPEG$_7$-5'-Gemcitabine monophosphate
di-mPEG$_3$-5'-Floxuridine monophosphate
di-mPEG$_7$-5'-Floxuridine monophosphate
mono-mPEG$_3$-5'-Floxuridine monophosphate
mono-mPEG$_7$-5'-Floxuridine monophosphate In vitro screening using Colon (HT29), Ovary (A2780), Lung (HOP62), and Prostate (DU145) tumor cell lines revealed that the tested conjugates possess growth inhibiting (GI$_{50}$) activity relative to Floxuridine.

The GI$_{50}$ values of mono-mPEG$_7$-Floxuridine monophosphate were $3.1 \times 10$- and $2.2 \times 10^{-6}$ in Hop62 and MCF7 respectively.

The conjugates showed no conversion (hydrolysis) to Floxuridine in the cell media during experimentation.

In Vitro Screening of PEG-Gemcitabine Monophosphate in Selected Human Cancer Cell Lines

TABLE 1

| Test Article | GI$_{50}$ (molar concentration) in Cell Line | | | | | | | |
|---|---|---|---|---|---|---|---|---|
| | DU145 | MCF7 | HT29 | COLO205 | HCT15 | A2780 | Hop62 | NCI/ADR-RES |
| Gemcitabine Mono (mPEG$_7$) | <1 × 10$^{-7}$ | 1.6 × 10$^{-7}$ | 3.2 × 10$^{-5}$ | 1.8 × 10$^{-7}$ | 2.3 × 10$^{-6}$ | 1.5 × 10$^{-7}$ | 2.4 × 10$^{-6}$ | 2.0 × 10$^{-6}$ |
| Gemcitabine Mono (mPEG$_3$) | <1 × 10$^{-7}$ | 1.6 × 10$^{-7}$ | 2.8 × 10$^{-5}$ | 1.6 × 10$^{-7}$ | 2.2 × 10$^{-6}$ | 1.5 × 10$^{-7}$ | 2.6 × 10$^{-6}$ | 1.7 × 10$^{-7}$ |
| Gemcitabine | Not attained | <1 × 10$^{-7}$ | 2.1 × 10$^{-6}$ | 1.4 × 10$^{-7}$ | 1.6 × 10$^{-7}$ | <1 × 10$^{-7}$ | 1.8 × 10$^{-6}$ | Not attained |

Similarly, activities of the compounds of the present invention may further be tested in following cell lines: HCT-116, HT-29 and CAKI-1, DLD-1, HCT-116, HT-29, SW-620, NCI-H23, NCI-H460, NCI-H522, PANC-1, HL-60, CCRF-CEM, K-562, As283, and RL cells.

Stability in Cell Culture Medium

The MCF-7 cell line was grown in RPMI 1640 medium containing 5% fetal bovine serum and 2 mM L-glutamine. Cells were inoculated into 24-well microtiter plates in 100 μL at 5×10$^3$ cells/well, in duplicate. After 24 h, test articles were added to the cells for 48 h, after which time the supernatant from each of the wells was collected and stored below −15° C. until HPLC analysis. The frozen samples were thawed and homogenized by vortex mixing. A 10 μl aliquot of the sample was transferred into a clean EPPENDORF tube. Samples were diluted with 190 μl methanol: water mixture (1:1, v/v). The tubes were vortex mixed and centrifuged for 10 min. The supernatant was transferred to HPLC vials and 10 μl volume of the sample was injected onto the HPLC system. A calibration curve was generated by spiking known amounts of floxuridine in cell culture media, because the retention time of floxuridine was decreased by the presence of medium (7.25 min vs. 9.2 min).

The concentration of floxuridine estimated in culture medium after cells were treated with floxuridine, and three floxuridine derivatives were 24.44, and below the assay detection level, respectively. Thus, floxuridine is not released from PEG-floxuridine in cell culture medium.

In Vitro Activity Studies

The aim was to determine the GI$_{50}$ values for PEG-floxuridine conjugates against a panel of cell lines, and based on previous data from Xenograft studies. The cells were exposed for 24 h, and cell viability assessed by using the Sulphorhodamine (SRB) assay. The test articles were solubilized in dimethylsulfoxide and were tested at four different molar (M) concentrations; 10$^{-4}$, 10$^{-5}$, 10$^{-6}$, 10$^{-7}$ M. GI$_{50}$ (the concentration needed to reduce the growth of treated cells to half that of untreated control cells) was calculated for each condition ([(T$_i$−T$_z$)/(C−T$_z$)]×100=50, where T$_i$, T$_z$, and C refer to absorbance values obtained from each tested concentration, time zero, and control treatment, respectively).

TABLE 2

| | Summary of HPLC data: peak area of measured floxuridine | | | | |
|---|---|---|---|---|---|
| Test Article | Peak Area | Calculated Concentration (μg/mL) | Dilution factor (10 μL sample diluted to 200 μL) | Total Calculated Concentration in the sample using dilution factor | Nominal concentration (μg/mL) |
| Floxuridine | 119819 | 1.211 | 20 | 24.22 | 24.6* |
| Floxuridine Mono (mPEG3) | — | NA | 20 | NA | NA |
| Floxuridine Mono (mPEG3) | — | NA | 20 | NA | NA |
| Floxuridine Di (mPEG3) | — | NA | 20 | NA | NA |

TABLE 3

GI$_{50}$ values (µM) of floxuridine and PEG conjugates in Human Tumor Cell lines of Prostate, Colon, Ovary, Lung and Breast.

| Compound | DU145 | MCF7 | HT29 | COLO205 | HCT15 | A2780 | Hop62 | NCI/ADR-RES |
|---|---|---|---|---|---|---|---|---|
| Floxuridine | 26 | 0.15 | 25 | ND | ND | 0.065 | 0.24 | ND |
| Floxuridine Mono (mPEG3) | 0.12 | 0.11 | >100 | 1.8 | 32 | 2.1 | >100 | <0.1 |
| Floxuridine Mono (mPEG7) | 0.13 | 0.13 | ~>100 | 1.9 | ~32 | 2.3 | >100 | <0.1 |
| Floxuridine Di (mPEG3) | >100 | >100 | >100 | ND | ND | >100 | >100 | ND |
| Floxuridine Di (mPEG7) | >100 | >100 | >100 | ND | ND | >100 | >100 | ND |
| ratio mono (mPEG3) vs flox | 0.005 | 0.7 | 4 | ND | ND | 32 | 417 | ND |
| ratio mono (mPEG7) vs flox | 0.005 | 0.9 | 4 | ND | ND | 35 | 417 | ND |
| ratio di(mPEG3) vs flox | 4 | 667 | 4 | ND | ND | 1538 | 417 | ND |
| ratio di(mPEG7) vs flox | 4 | 667 | 4 | ND | ND | 1538 | 417 | ND |

The mono-PEG-floxuridine monophosphate derivatives and/or floxuridine (no data for 3 cell lines) inhibited the growth of 5 of 8 cell lines with GI$_{50}$ values from the nM to low µM range (DU145 prostate, MCF-7 and NCI/Adr-Res breast, COL0205 colon, and A2780 ovarian). However, some of the GI$_{50}$ values should be interpreted with caution because the concentration range tested was not centered around the GI$_{50}$. The di-PEG derivatives were inactive in all cell lines tested. In conclusion, there is a range of sensitivities, and fold response to PEGylated floxuridines versus floxuridine.

In Vitro Cytotoxicity Assays

The objective of these studies were to determine the IC$_{50}$ values for PEG-floxuridine conjugates against floxuridine-resistant cell lines based on data from previous Xenograft studies. The cells were exposed for 72 h, and cell viability assessed by using the CellTiter-Glo assay.

TABLE 4

IC$_{50}$-values of floxuridine, NKT-10154, and NKT-10156 obtained from curve fits of data following exposure of resistant cell lines

| | IC$_{50}$ (nM) | | | Ratio vs floxuridine | |
|---|---|---|---|---|---|
| Cell Line | Floxuridine | Floxuridine Mono (mPEG3) | Floxuridine Mono (mPEG7) | Floxuridine Mono (mPEG3) | Floxuridine Mono (mPEG7) |
| HCT-116 | 32 | 56 | 48 | 2 | 2 |
| HT-29 | 90 | 87 | 76 | 1 | 1 |
| CAKI-1 | 110 | 145 | 157 | 1 | 1 |
| MIA PaCa-2 | 54 | 64 | 96 | 1 | 2 |

The PEGylated floxuridine monophosphate derivatives and floxuridine inhibited the growth of all of the tested cell lines with IC$_{50}$ values in the nM range. Like the previous study, some of the IC$_{50}$ values should be interpreted carefully because the concentration range tested was not centered around the IC$_{50}$.

Bi-Directional Permeability of PEG-Floxuridine Conjugates in Caco-2 and MDCK Cells

TABLE 5

Recovery and Apparent Permeability ($10^{-6}$ cm/s) of test compounds

| | | percent recovery | | $P_{app}$ | | Papp B-A/ | Absorption | Significant |
|---|---|---|---|---|---|---|---|---|
| | | A -> B | B -> A | A -> B | B -> A | Papp A-B | potential | efflux |
| floxuridine | Caco-2 | 75 | 91 | 0.75 | 1.47 | 2.0 | Low | No |
| | MDCK | 50 | 82 | <2.46 | <2.70 | ND | — | No |
| NKT-10154 | Caco-2 | 96 | 94 | <0.19 | <0.25 | ND | Low | No |
| | MDCK | 98 | 98 | <0.06 | <0.07 | ND | — | No |
| NKT-10156 | Caco-2 | 79 | 89 | 0.14 | 0.06 | 0.4 | Low | No |
| | MDCK | 100 | 90 | <0.06 | <0.08 | ND | — | No |
| Capecitabine | Caco-2 | 110 | 99 | 2.22 | 8.71 | 3.9 | High | Yes |
| | MDCK | 104 | 99 | 0.16 | 0.14 | 0.9 | — | No |

The absorption potential of the compounds was determined in Caco-2 and MDCK cells, where absorption is considered low if $P_{app}$ (A–B) is $<1.0\times10^{-6}$ cm/s. An orally bioavailable nucleoside analog, Capecitabine, showed high permeability across Caco-2 monolayers, but relatively poor permeability through MDCK monolayers. Floxuridine and PEGylated floxuridine compounds showed poor permeability through both cell lines. Floxuridine had poor analytical sensitivity compared to the other analytes (LOD was approximately 0.03 uM, compared to <0.01 uM, respectively).

Gemcitabine: In Vitro Stability Studies
Stability in Cell Culture Medium (LS-2007-016)

The MCF-7 cell line was grown in RPMI 1640 medium containing 5% fetal bovine serum and 2 mM L-glutamine. This cell lines was chosen because it was moderately sensitive to gemcitabine ($GI_{50}$~100 nM). Cells were inoculated into 24-well microtiter plates in 100 µL at $5\times10^3$ cells/well, in duplicate. After 24 h, test articles were added to the cells for 24 or 48 h, after which time the supernatant from each of the wells was collected and stored below –15° C. until LC/MS analysis.

Gemcitabine showed roughly 100-110% recovery in all media types. For PEG-gemcitabine, there are two "bins" of data: 60-80% recovery, versus 100% recovery of PEG-gemcitabine. Samples from RPMI+FBS, RPMI+FBS+ cells, and conditioned medium, where 10% FBS was a component, had 60-80% recovery, whereas RPMI alone or with "serum replacement" showed 100-120% recovery. Samples from PEG-gemcitabine incubated in PBS had approximately 80% recovery of test article at both time points. It is not clear why the stability of PEG-gem is lower in PBS versus RPMI medium. On a mM basis, about 80% of the mPEG3 or mPEG7 remains after 24 and 48 h, thus there is not a significant decrease over time. The <10% decrease in PEG-gemcitabine that is observable from time point 24 to 48 h is due to conversion to gemcitabine.

In Vitro Activity Studies

The objective was to determine the $IC_{50}$ values for PEG-gemcitabine conjugates against a panel of cell lines, and based on previous data from Xenograft studies. The cells were exposed for 24 h, and cell viability assessed by using the Sulphorhodamine (SRB) assay. The test articles were solubilized in dimethyl sulfoxide and were tested at four different molar (M) concentrations; $10^{-4}$, $10^{-5}$, $10^{-6}$, $10^{-7}$ M. $GI_{50}$ (the concentration needed to reduce the growth of treated cells to half that of untreated control cells) was calculated for each condition ($[(T_i-T_z)/(C-T_i)]\times100=50$, where $T_i$, $T_z$, and C refer to absorbance values obtained from each tested concentration, time zero, and control treatment, respectively).

TABLE 7

$GI_{50}$ values (µM) of gemcitabine and its PEG conjugates in Human Tumor Cell lines of Colon, Ovary, Lung and Breast.

| | DU145 | MCF7 | HT29 | COLO-205 | HCT15 | A2780 | Hop62 | NCI/ADR-RES |
|---|---|---|---|---|---|---|---|---|
| Gemcitabine Mono (mPEG7) | <0.1 | 0.16 | 32 | 0.18 | 2.3 | 0.15 | 2.4 | 2.0 |
| Gemcitabine Mono (mPEG3) | <0.1 | 0.158 | 28 | 0.16 | 2.2 | 0.15 | 2.6 | 1.7 |
| Gemcitabine | <<0.1 | <0.1 | 2.1 | 0.14 | 0.16 | <0.1 | 1.8 | nd |
| ratio mPEG7 vs gem | nd | 2 | 15 | 1 | 14 | 2 | 1 | nd |
| ratio mPEG3 vs gem | nd | 2 | 13 | 1 | 14 | 2 | 1 | nd |

The PEG-gemcitabine derivatives and gemcitabine inhibited the growth of most of the cell lines with $GI_{50}$ values from the nM to low μM range, except for HT-29. Some of the $GI_{50}$ values should be interpreted with caution because the concentration range tested was not centered around the $GI_{50}$. Adriamycin was used as a positive control.

In Vitro Cytotoxicity Assays

The objective of these studies was to determine the $IC_{50}$ values for PEG-gemcitabine conjugates against gemcitabine-resistant cell lines based on data from previous Xenograft studies. The cells were exposed for 72 h, and cell viability assessed by using the CellTiter-Glo assay.

nificant difference in cell growth after treatment with gemcitabine or the PEGylated derivatives. The PANC-1 pancreatic cell line, in contrast to BxPC-3, Capan-1, or MIA-PaCa-2, has been shown previously to be resistant in vitro to gemcitabine, and 4'-thio-FAC, a deoxycytidine sulfur- and fluoro-substituted analog (Zajchowski et al., (2005). Int J Cancer. 114(6), 1002-9).

Bi-Directional Permeability of PEG-Gemcitabine Conjugates in Caco-2 and MDCK Cells The absorption potential of the compounds was determined in Caco-2 and MDCK cells, where absorption is con-

TABLE 8

$IC_{50}$-values of gemcitabine, NKT-10238, and NKT-10239 obtained from curve fits of data following exposure of resistant cell lines.

| | $IC_{50}$ (nM) | | | Ratio vs gem | |
|---|---|---|---|---|---|
| Cell Line | Gemcitabine | mPEG3-Gem | mPEG7-Gem | mPEG3-Gem | mPEG7-Gem |
| HCT-116 | 1.9 | 2.9 | 4 | 2 | 2 |
| HT-29 | 111 | 755 | 6252 | 7 | 56 |
| CAKI-1 | 8.3 | 21 | 50 | 3 | 6 |
| MIA PaCa-2 | 26 | 76 | 84 | 3 | 3 |
| DLD-1 | 22 | 93 | 36 | 4 | 2 |
| SW-620 | 49 | 95 | 182 | 2 | 4 |
| NCI-H23 | 6.9 | 18 | 47 | 3 | 7 |
| NCI-H460 | 14 | 43 | 48 | 3 | 3 |
| NCI-H522 | 4.4 | 36 | 26 | 8 | 6 |
| PANC-1 | >1,000,000 | >1,000,000 | >1,000,000 | na | na |
| HL-60 | 1.7 | 2 | 2.6 | 1 | 2 |
| CCRF-CEM | 7 | 6.5 | 10 | 1 | 1 |
| K-562 | 697 | 914 | 1148 | 1 | 2 |
| AS283 | 124 | 408 | 398 | 3 | 3 |
| RL | 281 | 568 | 259 | 2 | 1 |

The PEG-gemcitabine derivatives and gemcitabine inhibited the growth of most of the cell lines with $IC_{50}$ values from the nM to low μM range, except for PANC-1 cells. Like the previous study, some of the $IC_{50}$ values should be interpreted carefully because the concentration range tested was not centered around the $IC_{50}$. Resistance was observed in one cell line, PANC-1 (mechanism unknown), and there was no significant difference in cell growth after treatment with gemcitabine or the PEGylated derivatives showed poor permeability through both cell lines.

sidered low if $P_{app}$ (A–B) is $<1.0 \times 10^{-6}$ cm/s. An orally bioavailable nucleoside analog, Capecitabine, showed high permeability across Caco-2 monolayers, but relatively poor permeability through MDCK monolayers. Gemcitabine and PEGylated gemcitabine compounds showed poor permeability through both cell lines.

TABLE 9

Recovery and Apparent Permeability ($10^{-6}$ cm/s) of test compounds

| | | percent recovery | | $P_{app}$ | | Papp B-A/ Papp A-B | Absorption potential | Significant efflux |
|---|---|---|---|---|---|---|---|---|
| | | A -> B | B -> A | A -> B | B -> A | | | |
| gemcitabine | Caco-2 | 90 | 89 | 0.3 | 0.42 | 1.4 | Low | No |
| | MDCK | 96 | 95 | 0.17 | 0.12 | 0.7 | — | No |
| mPEG3-Gem | Caco-2 | 78 | 90 | <0.06 | <0.08 | ND | Low | No |
| | MDCK | 91 | 96 | <0.06 | <0.08 | ND | — | No |
| mPEG7-Gem | Caco-2 | 74 | 86 | <0.06 | <0.08 | ND | Low | No |
| | MDCK | 94 | 96 | <0.06 | <0.08 | ND | — | No |
| Capecitabine | Caco-2 | 110 | 99 | 2.22 | 8.71 | 3.9 | High | Yes |
| | MDCK | 104 | 99 | 0.16 | 0.14 | 0.9 | — | No |

What is claimed is:

1. A compound having the following structure:

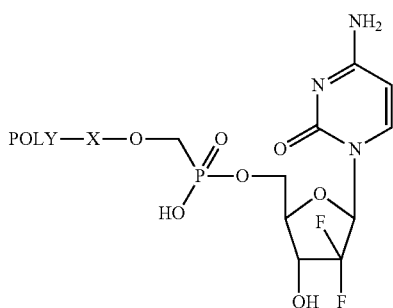

wherein:
X is a linker when present; and
POLY is a poly(ethylene oxide) oligomer having an end capping group selected from hydroxyl and methoxy end-capping groups.

2. The compound of claim 1, wherein the poly(ethylene oxide) oligomer is made of between 2 and 30 monomers.

3. The compound of claim 2, wherein the poly(ethylene oxide) oligomer is made of between 2 and 10 monomers.

4. The compound of claim 1, wherein the poly(ethylene oxide) oligomer is capped with a methoxy end-capping group.

5. The compound of claim 1, wherein X is an ether linker.

6. The compound of claim 1, wherein X is an ester or a phosphoester linker.

7. A composition comprising a compound of claim 1, and optionally, a pharmaceutically acceptable excipient.

8. A composition of matter comprising a compound of claim 1, wherein the compound is present in a dosage form.

9. A method of treating cancer, comprising administering a compound of claim 1 to a subject in need thereof.

10. The compound of claim 1, having the following structure

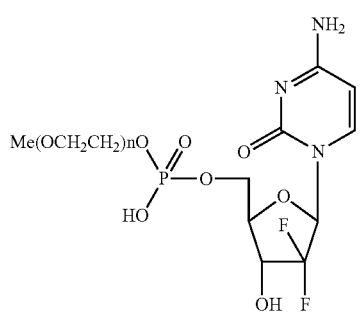

wherein n is selected from an integer from 2 to 10.

11. The compound of claim 10, wherein n is selected from 3 and 7.

12. The method of claim 9, wherein the cancer is selected from breast cancer, colon cancer, pancreatic cancer, lung cancer, and ovarian cancer.

* * * * *